United States Patent
Goswami et al.

(10) Patent No.: US 7,060,434 B2
(45) Date of Patent: Jun. 13, 2006

(54) PROBES FOR MYCTOPHID FISH AND A METHOD FOR DEVELOPING THE SAME

(75) Inventors: Usha Goswami, Goa (IN); Giacomo Bernardi, Santa Cruz, CA (US); Subhash Chander Goswami, Goa (IN); Robert K. Johnson, deceased, late of Charleston, SC (US); by Patricia Johnson, legal representative, Charleston, SC (US)

(73) Assignee: Council of Scientific & Industrial Research, New Delhi (IN)

( * ) Notice: Subject to any disclaimer, the term of this patent is extended or adjusted under 35 U.S.C. 154(b) by 726 days.

(21) Appl. No.: 09/782,604

(22) Filed: Feb. 14, 2001

(65) Prior Publication Data

US 2003/0143534 A1  Jul. 31, 2003

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.1; 435/91.2; 536/23.1; 536/23.5; 536/24.31

(58) Field of Classification Search .............. 435/6, 435/91.1, 91.2; 536/23.1, 23.5, 24.31, 24.33
See application file for complete search history.

(56) References Cited

U.S. PATENT DOCUMENTS 5,827,657 A * 10/1998 Herrnstadt et al. ............ 435/6

FOREIGN PATENT DOCUMENTS

DE   0 849 364 A1 *  6/1998
EP   WO-9205277 A1 *  4/1992

OTHER PUBLICATIONS

Foran (1991) The Journal of Experimental Zoology 259:1–8.*

Haygood et al. (1994)The Journal of Experimental Zoology 270:225–231.*

Lee et al.(1995) Journal Mol. Evol. 41:54–66.*

Yamaguchi et al. (2000) Molecular Phylogenetics and Evol. vol. 15, No. 1 Apr. pp. 103–114.*

* cited by examiner

*Primary Examiner*—Jeffrey Fredman
*Assistant Examiner*—Sally Sakelaris
(74) *Attorney, Agent, or Firm*—Foley & Lardner LLP

(57) ABSTRACT

The DNA probes produced by molecular cloning and the characterization of specific gene region sequences is provided, these can be used as genetic markers for the genes such as Cytochrome b (cyt b); Mitochondrial control region (D-Loop); Inter Transcribed Spacers (ITS2) and Rhodopsin (ROD), 12S rRNA and 16S rRNA in mesopelagic lantern fishes which are found in the mesopelagic zones of the oceans where the photic regime is of dim light and associate themselves with the oxygen minimum layer, it also includes the recombinant DNA techniques for the preparation of specific gene probes and sequences of species specific primers of lantern fishes, novel gene probes and novel oligonucleotides for amplification of myctophid genes are disclosed.

2 Claims, No Drawings

PROBES FOR MYCTOPHID FISH AND A METHOD FOR DEVELOPING THE SAME

FIELD OF INVENTION

This invention relates to the molecular cloning and characterization of specific gene region sequences. More particularly the invention relates to genetic markers which have been identified in several genes such as Cytochrome b (cyt b); Mitochondrial control region (D-Loop); Inter Transcribed Spacers (ITS2) and Rhodopsin (ROD) in a mesopelagic lantern fish which are found in the mesopelagic zones and associate themselves with the oxygen minimum layer. The invention is also concerned with the recombinant DNA techniques for the preparation of specific gene probes useful for identification of larval and adult life history stages of myctophids i.e. Lantern fishes. The invention also deals with construction of species specific primer sequences.

BACKGROUND OF THE INVENTION

Among the mesopelagic fishes, the lantern fishes (Family Myctophidae) are extremely common and numerous in both species and individuals in the open ocean midwaters of the world oceans. The myctophid fishes are generally found associated with the oxygen minimum layer of the midwaters and are active vertical migrators. They have adapted themselves to low oxygen conditions and low/dark light intensity conditions.

Most studies on midwater fish have been restricted to investigations of the oxygen minimum layer in the eastern tropical pacific and/or morphological adaptations (Kinzer et al. Deep Sea Research II, 40 (3): 783–800 (1993).

Little is known about the biology and ecology of this group particularly the dynamics of the interaction between mesozooplankton stocks and abundant migratory myctophids. The extreme oxygen deficiency of the Arabian Sea at mid depth has been well documented. Dissolved oxygen slowly increases below 1000 meter depth from about 0.2 ml per liter to 2.5 milliliter per liter at 2000 meter depth. Near the bottom at 3000 meter oxygen values average 3.5 ml per liter (SenGupta, R and S. W. A. Naqvi, Deep Sea Research, 31: 671–706, (1984).

The myctophid fish are adapted to low oxygen conditions and low/dark light intensity conditions. Their physiological adaptations to these varying abiotic and biotic factors have enabled them to survive in the vast sub-oxia below 150 meter depth zone.

The myctophids are strong vertical migrators and active swimmers. Most of them are black/dark brown in color and possess fluorescent organs called photophores. They constitute food for higher fishes of commercial importance such as Tuna, Sharks and marine mammals.

In the northern and western Arabian Sea itself the US GLOBEC Report No. 9 (1993) reported a biomass of about 100 million metric tonnes per year (present world fishery catch is around seventy million metric tonnes). Their dominance could be due to their ability to live in the suboxic middle depths and avoid predators.

Due to high protein content vast myctophid populations can form an excellent fish meal and poultry feed to support aquaculture and other farming activities. The myctophids can facilitate the assessment of water bodies, estimation of genetic resources, genetic variability and the level of gene flow between various stocks and populations in the world oceans.

Traditionally, various investigators including; Gunther, A. Report on the deep-Sea Fishes collected by H. M. S. Challenger during the years 1873–1876, Reprint 1963, Text volume, J. Cramer, Weinheim, Hafner, New York, 1–135 (1887); Gilbert, Proceedings of the U.S. National Museum, 48: 305–380 (1915), and Fraser-Brunner, proceedings of the Zoological society of London, 118 (4) 1019–1106 (1949), classified the species in the family Myctophidae by using differences in the position and numbers of photophores located on head and body of fish.

While photophore differences are still of primary importance, the morphometry is also used statistically (Paxton, Bulletin of the natural history museum of Los Angeles County, Science, No. 13 (1972).

The methods are incompetent to identify the closely allied species, populations and the life history stages. This is the major bottleneck for the proper identification, population dynamics and stock assessment of these fishes leaving their systematics unjustified.

There are several reasons for this confusion. In the first place, the fish are particularly fragile and easily damaged in collecting nets, so most specimens collected tend to be in poor condition.

Second, the group contains many morphologically similar species from all parts of the world.

Third though there is only small amount of variability in most characters, there is enough in some cases for similar species to overlap even in those characters wherein they differ most significantly (Zahuranec, B, Zoogeography and Systematics of the lantern fishes of the genus *Nannobrachium* (Lampanyctini: Myctophidae) PhD Thesis, Scripps Institution of Oceanography, University of California, San Diego, 1995).

The problems have been compounded since specimens of many forms have not been numerous. It is difficult to collect ample material for the taxonomic studies using the existing conventional methods.

The midwater habitat of the fish make them a uncommon and difficult material to get for work as special gears are required on board of ship.

The mesopelagic habitats of the north Arabian sea support rich and varied fauna. Most of these fishes belong to Myctophidae, Gonostomitids, Sternoptychids etc. The richness of this resource in the mesopelagic regime of the oceans all the world over has been well documented (Boltachev, A. R. J. Ichthyol, 27 (4): 539–547 (1987); Hussain and Ali Khan, Deep Sea Research, 34 (7A): 1293–1299 (1987); Alikhan and Aftab, Marine Research, 2 (1–2): 1–9 (1993).

US Globec, 1993 has reported a biomass of 100 million Tonnes of Myctophids in the Arabian Sea believed to be constituted by *Benthosema pterotum* and *Diaphus* sp. The true identity of stocks is, however, unknown.

In class Pisces there is a large body of population genetic data available on CD-ROMs and fish data bases (Agustin and Palomares, 5th International Symposium on Genetics in aquaculture, 19–25, 1994). However, very little information pertains to the families of lantern fishes. There is only one paper on myctophids by Afanas-yev et al. J. Ichthiology, 30 (1):28–37 (1990).

The earlier workers have described genetic diversity amongst conspecific and closely related species using protein electrophoresis. However, in the recent years, the molecular techniques using DNAs as the genetic markers have almost replaced these traditional methods with many shortcomings and providing information about only 1% of the genome.

Several workers have applied the new methods of DNAs for quantifying genetic relatedness among group of fish in stock assessments among wild and cultured populations and in studies of taxonomy and population genetic (Datta et al., Gene, 62: 331–336. 1988; Devlin et al. Canadian Journal of Fishery and Aquatic Sciences, 48 (9): 1606–1612,1991; Berson et al. Molecular Microbiology, 5 (9), 2261–2264, 1991; Martinez et al. Genome, 36: 1119–1123, 1993; Du Jun et al. DNA and cell Biology, 12 (8): 739–751, Cytogenetic and cellular genetics, 65: 233–237, 1993; Pogson et al. Genetics, 139: 375–3851994 and Carr et al. Molecular Ecology, 4:79–88, 1995.

There is a great lacunae in our knowledge of myctophid resource and stock assessment using genetic techniques. The only information so far available in related isozyme studies on 3 species endemic to the eastern pacific (Afanas-yev et al. 1990).

There is absolutely no literature available on genetic assessment of stocks from the other oceans.

A judicious exploitation and resource management requires proper identification of the larval and adult stages of huge myctophid populations in the world oceans. The genetic resource assessment, species identification, characterzation of life history stages, estimation of genetic variability and level of gene flow between various stocks for proper utiliztion of this vast fishery potential and for assessment and evaluation of trophic dynamics at the top end of the marine food chain.

Various authors have described methods of making DNA probes and their use as genetic markers in various organisms using mostly cDNA approach. Some patents pertain to improvement of DNA amplification related methods and formulation of different primers.

Weissman et al. 1983 patented Method for cloning genes (U.S. Pat. No. 4,394,443 published on Jul. 19, 1983). Mullis et al. In U.S. Pat. No. 4,683,195 published on Jul. 28, 1987 describe process for amplifying, detecting, and/or cloning nucleic acid sequences. The methods provided recombinant clones coding for human histocompatibility antigens, in particular clones for HLA-B antigens. The recombinant DNA expression system is developed for use in control of larval and adult insects and conferring pesticide resistance to crop plants.

Erlich et al. (U.S. Pat. No. 5,314,809 published on May 24, 1994) provide methods for enhanced specificity and sensitivity of nucleic acid amplification. The methods are simplified nested amplification procedures wherein both inner and outer primer pairs are present in the amplification reaction mixture.

Grosz, et al. In U.S. Pat. No. 5,340,728 published on Aug. 23, 1994 describe method for amplification of targeted segments of nucleic acid using nested polymerase chain reaction. Nuovo et al. (1996) in U.S. Pat. No. 5,538,871, published on Jul. 23, 1996 describe in improved In situ polymerase chain reaction. Barry et al. In U.S. Pat. No. 5,574,145 published on Nov. 12, 1996 isolated nucleic acid molecules targeted to the region intermediate to the 16 S and 23 S rRNA genes useful as probes for determining bacteria. They describe a method for generating DNA probes specific for an organism and capable of distinguishing in a non-empirical manner between species.

Cossart et al. (U.S. Pat. No. 5,523,205 published on Jun 4, 1996) describe DNA probes specific for hemolytic listeria bacteria. Trent et al. In the U.S. Pat. No. 5,693,464 published on Dec. 2, 1997 report rapid reproducible procedures for generating chromosome region-specific (CRSPs) for diagnostic and research applications.

Scott and Tomita (1998) give uses of cytochrome P450. Sub.Ipr gene (U.S. Pat. No. 5,734,086, published on Mar 31, 1998). Harris et al. (1998, U.S. Pat. No. 5,849,544, Dec. 15, 1998) give method of characterization and provide method for the detection of diagnostic base sequences in one or more nucleic acids contained in a sample.

Jeffreys et al (1998, U.S. Pat. No. 5,853,989, published on, Dec 29, 1998) describe method of characterisation of genomic DNA. They used primers which selectively prime specific type of internal repeat unit in a tandemly repeated region. Ryder et al. (1998, U.S. Pat. No. 5,786,183, published on Jul 28, 1998) give methods of enhancing nucleic acid amplification. Dandliker et al. (1998, U.S. Pat. No. 5,707,813, published on Jan 13, 1998) report nucleic acid probes and methods. Kuhns (1999, U.S. Pat. No. 5,981,171, published on Nov. 9, 1999) describe diagnostic assays using nucleic acid probes. He describes methods and compositions for a rapid quantitative nucleic acid hybridization assay fpr detecting a DNA or RNA sequence in a biological sample.

Caetano-Anolles (1999, U.S. Pat. No. 5,962,221, published on Oct. 5, 1999) give oligonucleotide constructs and methods for the generation of sequence signatures from nucleic acids.

Bebbington et al (1999, U.S. Pat. No. 5,891,693, published on Apr. 6, 1999) describe recombinant DNA methods vectors and host cells. Rothschild et al. In U.S. Pat. No. 5,939,264 published on Aug 17, 1999) describe genetic markers in pigs for reproductive traits using polymorphism in the reproductive genes.

Molecular cloning and characterization of a further gene sequences coding for human relaxin is given in U.S. Pat. No. 4,758,516 by Hudson et al. published on Jul. 19, 1988.

Some patents related to the genes reported by us is available on humans and other organisms. Aguirre et al. (1998) developed progressive rod-cone degeneration disease genetic markers and assays in a canine (U.S. Pat. No. 5,804,388). Reports on diagnosis of hereditary retinal degenerative diseases is given by Dryja et al. In U.S. Pat. No. 5,262,529 published on Nov. 16, 1993 They developed a probe for identifying region of photoreceptor protein of humans and also made the primers. Dryja et al in Mar. 1996, U.S. Pat. No. 5,498,521 published on Mar. 12, 1996 later report the method which involves analyzing the DNA of the subject to determine the presence or absence of a mutation in a gene for photoreceptor protein. Shassere, et al. (1997 U.S. Pat. No. 5,698,398 published on Dec. 16, 1997) disclosed quality control compositions suitable as sample specimens to measure performance of DNA probe tests which determine cytogenetic abnormalities, such as chromosome copy number, of cells in a tissue sample.

However, all of these are related to making cDNA probes and the work is mostly on humans, canines, bacteria and other organisms, mostly of terrestrial origin.

No patent is available on fish DNA probes and sequences as genetic markers particularly in the myctophid fish. Nor are primer sequences designed for these fishes.

Earlier Mitochondrial DNA control region and Ribosomal Internal transcribed spacer (ITS2) are used for systematic relationships. Reed K. M, et al. (1998) studied sequence analysis of the mitochondrial DNA control region of ciscoes (genus *Coregonus*) with taxonomic implications for the Great Lakes species flock.

Molecular cloning of rod opsin (rhodopsin) cDNA from retinas of various teleost fishes, octopus, squids, shrimps, Lamprey and screening of cDNA libraries of rhodopsin is done by several workers (O'Brien and Al-Ubaidi, M. R., Gene, 193 (2): 141–150; Crescitclli, F, et al. Journal of Comparative Physiology, 1985: 157 (3): 323–333; Tsai, H. J. et al., Biochemical molecular Biology, 109, 91: 81–88; Hara-Nishimura et al. FEBS-LETT, 317 (1–2): 5–11, 1993). Crandall, K. A. and Hillis, D. M. Nature, 387 (No. 6634), 667–668,1997, describe rhodopsin protein evolution in the dark in cave dwelling cray fish. Fitzgibbon, j et al., Gene, 1995,164 (2), 273–277. Harada, Y et al. Journal of Biochemistry, 110 (4), 501–507,1991 report synthesis and expression of rhodopsin gene in Octopus. But all these reports deal with the protein rhodopsin, not much has been said about its gene even in these species.

Douzery E, et al. Molecular Biology and Evolution, 14(11):1154–66 (1997) use the mitochondrial control region of Cervidae: evolutionary patterns and phylogenetic content. Barreto G, et al. American Journal of Human Genetics 58(3):609–16 (1996) report Mitochondrial D-loop "signatures" produced by low-stringency single specific primer PCR constitute a simple comparative human identity test. Brown JR, et al. Genetics. 142(2):525–35. 1996 describe Length variation, heteroplasmy and sequence divergence in the mitochondrial DNA of four species of sturgeon (Acipenser). Lee W J, et al. J Mol Evol. July 1995;41(1):54–66 report structure and evolution of teleost mitochondrial control regions. No reports of DNA probes for genetic marking of any marine species is come across.

Jobst J, et al (1998) give information on Molecular evolution of the internal transcribed spacers (ITS1 and ITS2) and phylogenetic relationships among species of the family Cucurbitaceae. Odorico D M, et al. (1997) describe Variation in the ribosomal internal transcribed spacers and 5.8S rDNA among five species of Acropora (Cnidaria; Scleractinia): patterns of variation consistent with reticulate evolution. Despres L, et al (1995) describe ITS2 ribosomal RNA indicates Schistosoma hippopotami is a distinct species. Crabtree M B, et al. (1995) study development of a species-diagnostic polymerase chain reaction assay for the identification of Culex vectors of St. Louis encephalitis virus based on interspecies sequence variation in ribosomal DNA spacers. Mukhamedov R S, et al. (1994) report [Nucleotide sequence of internal transcribed spacers and 5.8S rDNA for the ribosomal operon from alfalfa Medicago sativa and cotton Gossypium hirsutum L]. No reports of DNA probes in open ocean marine fish are seen.

Goswami and Bernardi (1999) described nucleotide gene sequences of 16 S and 12 S genes of five myctophid species viz: *Tarletonbeania crenularis; Protomyctophum crockeri; Lampanyctus regalis; Diaphus theta; Stenobrachius leucosparus* in the National center of Biotechnology information GenBank. These sequences were published on 20 Apr., 1999 and can be screened at www period ncbi period nlm period nih period gov Genbank databases. The respective accession numbers are AF134250; AF134249; AF134248; AF134247; AF134246; AF134245; AF134244; AF134243; AF134242 and AF134241.

As such, in order to obcriate the draw backs listed in the use of conventional taxonomic methods for identification of open ocean midwater fish, the applicants developed a novel method and approach, using molecular biology.

The invention relates to the molecular cloning and characterization of specific gene region sequences. More particularly the invention relates to genetic markers which have been identified in several genes such as Cytochrome b (cyt b); Mitochondrial control region (D-Loop); Internal Transcribed spacer between nuclear ribosomal genes (ITS2) & Rhodopsin gene of visual pigments (Rod) and mitochondrial ribosomal RNA genes for myctophid fishes.

As discussed above, prior art patents and reports deal with different groups of organisms. The invention on the other hand concerns an economically important group of open ocean midwater fish found in all the world oceans which has adapted itself to the oxygen minimum conditions and to low/dark light intensities for vision, the genetic information of which has not been reported so far.

The genomic DNA probes are sequence specific and are ideal for identification of complimentary regions of species specific genes. Cytochrome b is an important component of mitochondrial electron transport chain and plays important role in respiratory physiology (William, F. Ganong, Chapter 17 199–235 in Review of medical physiology pp. 599; 1977). The gene encoding cytochrome b, termed Cyt b of myctophid fishes plays an important role in adaptations and survivals of these fishes in the suboxic regions.

The Rod gene encoding for rhodopsin of the retinal rods is important for adapations of these fishes to varying light intensities which varies with the depth.

The mitochondrial control region D-Loop an Internal transcribed spacer ITS2 gene regions are highly prone to rapid mutations and can be suitable gene candidates for identification of variants at the intra species and population level.

The invention discloses species specific DNA probes for detection of genes such as cyt b, Rod, D-Loop, ITS2. This invention is useful for identification of early and adult life history stages of myctophids i.e. Lantern fishes.

This is the first report of preparation of DNA probes useful for molecular genetic identification of myctophid fish. Novelty of the invention is in use of novel gene region DNA probes for identification of eggs and early larvae of mesopelagic fish which live in oxygen minimal and low light conditions.

OBJECTS OF THE INVENTION

The main object of the invention is to provide an effective method for identifying stock and population of myctophids.

Another object is to provide a method using polymerase chain reaction with specific primers to detect and quantify the expression of genes like cytochrome b, Rod, D-Loop, $ITS_2$ etc. in myctophid fishes.

Another object of the present invention is to develop specific DNA probes for identification of populations of mesopelagic fish of the type myctophids.

Yet another object of the invention is to develop DNA probes comprising specific nucleotide sequences which specifically can detect mitochondrial genes such as Cyt b, D-Loop in myetophid fishes.

Still another objective is to develop DNA probes comprising specific nucleotide sequences which specifically can detect nuclear genes such as Rod and ITS2 in fishes.

Another objective of the invention is design specific primers for specific gene regions.

Still another object is to develop kits containing primer sets.

DETAILED DESCRIPTION OF THE INVENTION

The present invention seeks to overcome the drawbacks inherent in the prior art by providing the highly efficient and selective means for identifying the stocks and populations of myctophids using specific nucleic acid probes of certain genes. As used herein the, term 'probes' and 'probe' are used to designate the collection of DNA segments produced by amplification of specific regions.

Accordingly, the invention provides a method for development of DNA probes for myctophids which comprises:

(i) Extracting the DNA from the tissue of an identified myctophid fish, (ii) Selecting primers for species and population level, (iii) Amplifying the extracted DNA using polymerase chain reaction (PCR) using the selected primers, (iv) Eluting the amplified DNA from the PCR reactions, (v) Cycle sequencing of 5 mu L. eluted DNA using single primer, (vi) Purifying extension products, (vii) Sequencing on acrylamide gel in an automated sequencer.

(viii) Cloning a part of the eluted DNA (TV) from the resulting PCR product into a suitable vector, and growing in competent transformed host cells, (ix) Purifying recombinant plasmid DNA having the cloned gene probes from the transformed host cells.

(x) Checking purity and specificity of the cloned DNA probe insert, (xi) Confirming the molecular size of the DNA probe insert, (xii) Sequencing of the cloned DNA probe.

(xiii) Comparing the DNA sequences of the prepared DNA probe with the sequences of the same gene region done in the automated sequencer, (xiv) Comparing the DNA sequence of the DNA probes using "BLAST" program against the known sequences of similar genes in the genome data bases.

Thus, the invention provides nucleoticle sequences, primers and probes which exhibit myctophid specificity in nucleic acid amplification reactions. The invention relates to nucleotide sequences specific to mitochondrial genes in myctophid fishes. The invention also provides nucleotide sequences specific for the nuclear genes of myctophid fishes. Thus, the invention provides oligonucleotide primers that can be used for amplification of target sequence in myctophid fishes. These primers can amplify specific regions of gene by PCR.

In an embodiment the mitochondrial genes are Cyt b and D-loop genes.

In another embodiment the nuclear genes are Rod and ITS-2 genes.

In yet another embodiment the myctophid fishes are selected from the group comprising the steps of *Stenobrachius leucospara, Diaphus theta, Protomyctophum crockeri, Tarletonbeania crenularis, Lampanyctus regalis Symbolophorus* sp., *Triphoturus* sp. and *Lampanyctus* sp.

In still another embodiment the primer set (forward and backward primers) used for amplification and detection of Cyt b gene contains oligonucleotides with the sequences (SEQ ID NOS 1–2):

```
CYT1:    5' TGA YTT GAA RAA CCA YCG TTG 3'

CYT2:    5' CTC CAR TCT TCG RYT TAC AAG 3'
```

In another embodiment (forward and backward primers) used for reamplification and detection of Cyt b gene contains oligonucleotides with the sequences (SEQ ID NOS 3 and 2):

```
CBI-L:   5' CCA TCC AAC ATC TCA GCA TGA TGA AA 3'

CYT2:    5' CTC CAR TCT TCG RYT TAC AAG 3'
```

In another embodiment the primer set (forward and backward primers) used for PCR amplification and detection of D-Loop gene contains oligonucleotides with the sequences:

```
PRO-L:
5' CTA CC 3'

D-LOOP H:
5' CCT GAA GTA GGA ACC AGA TG 3'    (SEQ ID NO 4)
```

In another embodiment (forward and backward primers) used for PCR amplification of ITS2 gene contains oligonucleotides with the sequences SEQ ID NOS 5–6):

```
ITS2-F:    5' CTA CGC CTG TCT GAG TGT C 3'

ITS2-R:    5' ATA TGC TTA AAT TCA GCG GG 3'
```

In yet another embodiment the primer set (forward and backward primers) used for PCR amplification of Rhodopsin gene Rod contains oligonucleotides with the sequences SEQ ID NOS 7–8):

```
ROD-R:   5' TCT TTC CGC AGC ACA ACG TGG 3'

ROD-F:   5' CAT ATG AAT ACC CTC AGT ACT ACC 3'
```

In still another embodiment the primer set (forward and backward primers) used for PCR amplification of 12S RNA gene contains oligonucleotides with the sequences SEQ ID NOS 9–10):

```
12 SA-L:   5' AAA CTG GGA TTA GAT ACC CCA CTA T 3'

12 SB-H:   5' AGA GTG ACG GGC GGT GTG T 3'
```

In another embodiment the primer set (forward and backward primers) used for PCR amplification of 16S RNA gene contains oligonucleotides with the sequences (SEQ ID NOS 11–12):

```
16 SAR-L:  5' CGC CTG TTT ATC AAA AAC AT 3'

16 SBR-H:  5' CCG GTC TGA ACT CAG ATC ACG T 3'
```

In yet another embodiment the vector used for cloning was Bluescript KS⁻ phagemid.

In still another embodiment the vector used for cloning had ampicillin resistance gene for selection.

In another embodiment the vector used for cloning had Lac Z gene for blue white colony selection.

In another embodiment the Col E 1 was the origin for replication of phagemid in the absence of helper phage.

In another embodiment F 1 (–) origin for recovery of antisense strand of lac Z gene when a host strain containing the bluescript II phagemid (FIG. 1).

In another embodiment the host cells used for transformation were *E. coli* blue bacteria (Bacteria Strain XL 1 blue) XL1-Blue: F'::Tn10,pro A⁺B⁺ lacI^q
(lacZ)M15/recA1endA1gyrA96(Nal^r)thi hsdR17($r_k^-m_k^+$) supE44relA1 lac.

The invention also relates to specific DNA sequences for the cloned DNA probe inserts for the Cyt b, D-Loop, Rod, ITS2 genes. The invention provides species specific primer sequences for amplification and detection of Cyt b, D-Loop, Rod, ITS2, 12S RNA and 16 S RNA genes of *Stenobrachius leucopsarus* (SLMB) myctophid fish. The sequences of the species specific primer 12S rRNA -H and 12S rRNA -L of *Stenobrachius leucopsarus* (SLMB) designed were such as (SEQ ID NOS 13–14):

```
12S-H    5' CCC ACT CAC TGC TAA CTC C 3'
12S-L    5' GGC TAA CTA CAA TCA TCT GCT 3'
```

The sequences of the species specific primer 16S rRNA -H and 16S rRNA -L of *Stenobrachius leucopsarus* (SLMB) designed were such as (SEQ ID NOS 15–16):

```
16S-H    5' TAG GCA TAA CGG CTC TGG 3'
16S-L    5' CTA CTA CAC CTC AAC TAC ATC T 3'
```

The sequences of the species specific primer Cyt -H and Cyt -L of *Stenobrachius leucopsarus* (SLMB) designed were such as (SEQ ID NOS 17–18):

```
Cyt-H    5' GCT CGG GCT GCT GGA ATC TT 3'
Cyt-L    5' CAA CCT CAT CTG TCG TAA AC 3'
```

The sequences of the species specific primer ITS2-H and ITS2-L (Forward) of *Stenobrachius leucopsarus* (SLMB) designed were such as (SEQ ID NOS 19–20):

```
ITS2-H   5' ATA CTC TGC GGA CAT ACT TGA CTG 3'
ITS2-F   5' ACT TGA CTG ACC TTC TTA CT 3'
```

The sequences of the species specific primer Pro-L and D Loop -H of *Stenobrachius leucopsarus* (SLMB) designed were such as (SEQ ID NOS 21–22):

```
Pro-L    5' CAG TCT CGT CAA ACC AAG TCA AAC 3'
D loop-H 5' ATA ATC ATC CAG CAT AAA CAC AC 3'
```

The sequences of the species specific primer ROD -L and ROD-H of *Stenobrachius leucopsorus* (SLMB) designed were such as (SEQ ID NOS 23–24):

```
ROD-L    5' CCT GGT AGA GTT CGC CGT CA 3'
ROD-H    5' CGT GTT CCT TAT CAT TGT GCC T 3'
```

The sequences of the species specific primer 16S rRNA -H and 16S rRNA-L of yet another myctophid *Lampanyctus regalis* (LRMB) designed were such as (SEQ ID NOS 25–26):

```
16S-H    5' TCG TAG TTC AGC AGT CAG 3'
16S-L    5' CAC CAG CCA AGT ATG TTT CTC 3'
```

The sequences of the species specific primer 12S rRNA -H and 12S rRNA -L of yet another myctophid *Lampanyctus regalis* (LRMB) designed were such as (SEQ ID NOS 27–28):

```
12S-H    5' GCC TCC ATC ATC CCT CAC CTT AC 3'
12S-L    5' CTA TTC GCC TCG CTC AGA C 3'
```

The sequences of the species specific primer 16S rRNA -H and 16S rRNA -L of yet another myctophid *Diaphus theta* (DTMB) designed were such as SEQ ID NOS 29–30):

```
16S-H    5' CTC CGT CCG TCT CGC CTC TG 3'
16S-L    5' AAA TCC GCC CTT ATG TGT GTT C 3'
```

The sequences of the species specific primer 12S rRNA -H and 12S rRNA -L of yet another myctophid *Diaphus theta* (DTMB) designed were such as (SEQ ID NOS 31–32):

```
12S-H    5' CAT CGG CTT GCT CTA TTC CTT G 3'
12S-L    5' TCT ATC GGC GGC GTA TCA C 3'
```

The sequences of the species specific primer 16S rRNA -H and 16S rRNA -L of yet another myctophid *Tarletonbaenia crenularis* (TCMB) designed were such as (SEQ ID NOS 33–34):

```
16S-H    5' GGC GAT TCT ACG GCA CGG GCG 3'
16S-L    5' AAA CTG GTC CTC AAC TAT GTC A 3'
```

The sequences of the species specific primer 12S rRNA -H and 12S rRNA -L of yet another myctophid *Tarletonbaenia crenularis* (TCMB) designed were such as (SEQ ID NOS 35–36):

```
12S-H    5' CCG ATT CAG CCA CGA TTC CCT C 3'
12S-L    5' CCT AAA GCC CAG ATA ACT ACA 3'
```

The sequences of the species specific primer 16S rRNA -H and 16S rRNA -L of yet another myctophid *Protomyctophum crockeri* (PCMB) designed were such as (SEQ ID NOS 37–38):

```
16S-H    5' CGT GTT CTG ATG ATG ATG TGC T 3'
16S-L    5' ATT CCT TCC TCT TAG TAT G 3'
```

The sequences of the species specific primer 12S rRNA -H and 12S rRNA -L of yet another myctophid *Protomyctophum crockeri* (PCMB) designed were such as (SEQ ID NOS 39–40):

```
12S-H   5' GCT GAA CTT ACT ATG CCC TAG T 3'

12S-L   5' CCG ATT GAC GCC GAA CTA TG 3'
```

TABLE 1

Forward primer (SEQ ID NO: 18) designed for cytochrome b gene of *Stenobrachius leucopsarus* (slmb primer cyt L) with 5' to 3' end sequences (SENSE) and summaries of oligonucleotide and structural analyses.

TABLE 2

Backward primer (SEQ ID NO: 17) designed for cytochrome b gene of *Stenobrachius leucopsarus* (slmb primer cyt H) with 5' to 3' end sequences (ANTISENSE) and summaries of oligonucleotide and structural analyses.

TABLE 3

Forward primer (SEQ ID NO: 20) designed for Internal Transcribed Spacer (ITS2) of *Stenobrachius leucopsarus* (slmb primer ITS2 F) with 5' to 3' end sequences (SENSE) and summaries of oligonucleotide and structural analyses.

TABLE 4

Backward primer (SEQ ID NO: 19) designed for Internal Transcribed Spacer (ITS2) of *Stenobrachius leucopsarus* (slmb primer ITS2-H) with 5' to 3' end sequences (ANTISENSE) and summaries of oligonucleotide and structural analyses.

TABLE 5

Forward primer (SEQ ID NO: 21) designed for mitochondrial Control region d-Loop of *Stenobrachius leucopsarus* (slmb primer pro-L) with 5' to 3' end sequences (SENSE) and summaries of oligonucleotide and structural analyses.

TABLE 6

Backward primer (SEQ ID NO: 22) designed for mitochondrial Control region d-Loop of *Stenobrachius leucopsarus* (slmb primer D loop -H) with 5' to 3' end sequences (ANTISENSE) and summaries of oligonucleotide and structural analyses.

TABLE 7

Forward primer (SEQ ID NO: 23) designed for Rhodopsin gene region of *Stenobrachius leucopsarus* (slmb primer ROD-L) with 5' to 3' end sequences (SENSE) and summaries of oligonucleotide and structural analyses.

TABLE 8

Backward primer (SEQ ID NO: 24) designed for Rhodopsin gene region of *Stenobrachius leucopsarus* (slmb primer ROD -H) with 5' to 3' end sequences (ANTISENSE) and summaries of oligonucleotide and structural analyses.

TABLE 9

Forward primer (SEQ ID NO: 26) designed for mitochondrial 16S ribosomal RNA region of *Lampanyctus regalis* (LRMB primer 16 S-L) with 5' to 3' end sequences (SENSE) and summaries of oligonucleotide and structural analyses.

TABLE 10

Backward primer (SEQ ID NO: 25) designed for mitochondrial 16S ribosomal RNA region of *Lampanyctus regalis* (LRMB primer 16 S -H) with 5' to 3' end sequences (ANTISENSE) and summaries of oligonucleotide and structural analyses.

TABLE 11

Forward primer (SEQ ID NO: 28) designed for mitochondrial 12 S ribosomal RNA region of *Lampanyctus regalis* (LRMB primer 12 S-L) with 5' to 3' end sequences (SENSE) and summaries of oligonucleotide and structural analyses.

TABLE 12

Backward primer (SEQ ID NO: 27) designed for mitochondrial 12 S ribosomal RNA region of *Lampanyctus regalis* (LRMB primer 12 S -H) with 5' to 3' end sequences (ANTISENSE) and summaries of oligonucleotide and structural analyses.

TABLE 13

Backward primer (SEQ ID NO: 29) designed for mitochondrial 16 S ribosomal RNA region of *Diaphus theta* (DTMB primer 12 S -H) with 5' to 3' end sequences (ANTISENSE) and summaries of oligonucleotide and structural analyses.

TABLE 14

Forward primer (SEQ ID NO: 30) designed for mitochondrial 16 S ribosomal RNA region of *Diaphus theta* (DTMB primer 12 S-L) with 5' to 3' end sequences (SENSE) and summaries of oligonucleotide and structural analyses.

TABLE 15

Backward primer (SEQ ID NO: 31) designed for mitochondrial 12 S ribosomal RNA region of *Diaphus theta* (DTMB primer 12 S -H) with 5' to 3' end sequences (ANTISENSE) and summaries of oligonucleotide and structural analyses.

TABLE 16

Forward primer (SEQ ID NO: 32) designed for mitochondrial 12 S ribosomal RNA region of *Diaphus theta* (DTMB primer 12 S-L) with 5' to 3' end sequences (SENSE) and summaries of oligonucleotide and structural analyses.

TABLE 17

Backward primer (SEQ ID NO: 33) designed for mitochondrial 16 S ribosomal RNA region of *Tarletonbeania crenularis* (TCMB primer 16 S-H) with 5' to 3' end sequences (ANTISENSE) and summaries of oligonucleotide and structural analyses.

TABLE 18

Forward primer (SEQ ID NO: 24) designed for mitochondrial 16 S ribosomal RNA region of *Tarletonbeania crenularis* (TCMB primer 16 S-L) with 5' to 3' end sequences (SENSE) and summaries of oligonucleotide and structural analyses.

TABLE 19

Backward primer (SEQ ID NO: 35) designed for mitochondrial 12 S ribosomal RNA region of *Tarletonbeania crenularis* (TCMB primer 12 S-H) with 5' to 3' end sequences (ANTISENSE) and summaries of oligonucleotide and structural analyses.

TABLE 20

Forward primer (SEQ ID NO: 36) designed for mitochondrial 12 S ribosomal RNA region of *Tarletonbeania crenularis* (TCMB primer 12 S-L) with 5' to 3' end sequences (SENSE) and summaries of oligonucleotide and structural analyses.

TABLE 21

Backward primer (SEQ ID NO: 37) designed for mitochondrial 16 S ribosomal RNA region of *Protomyctophum crockeri* (PCMB primer 16 S-H) with 5' to 3' end sequences (ANTISENSE) and summaries of oligonucleotide and structural analyses.

TABLE 22

Forward primer (SEQ ID NO: 38) designed for mitochondrial 16 S ribosomal RNA region of *Protomyctophum crockeri* (PCMB primer 16 S-L) with 5' to 3' end sequences (SENSE) and summaries of oligonucleotide and structural analyses.

TABLE 23

Backward primer (SEQ ID NO: 39) designed for mitochondrial 12 S ribosomal RNA region of *Protomyctophum crockeri* (PCMB primer 12 S-H) with 5' to 3' end sequences (ANTISENSE) and summaries of oligonucleotide and structural analyses.

TABLE 24

Forward primer (SEQ ID NO: 40) designed for mitochondrial 12 S ribosomal RNA region of *Protomyctophum crockeri* (PCMB primer 12 S-L) with 5' to 3' end sequences (SENSE) and summaries of oligonucleotide and structural analyses.

TABLE 25

Backward primer (SEQ ID NO: 15) designed for mitochondrial 16 S ribosomal RNA region of *Stenobrachius leucopsarus* (SLMB primer 16 S-H) with 5' to 3' end sequences (ANTISENSE) and summaries of oligonucleotide and structural analyses.

TABLE 26

Forward primer (SEQ ID NO: 16) designed for mitochondrial 16 S ribosomal RNA region of *Stenobrachius leucopsarus* (SLMB primer 16 S-L) with 5' to 3' end sequences (SENSE) and summaries of oligonucleotide and structural analyses.

TABLE 27

Backward primer (SEQ ID NO: 13) designed for mitochondrial 12 S ribosomal RNA region of *Stenobrachius leucopsarus* (SLMB primer 12 S-H) with 5' to 3' end sequences (ANTISENSE) and summaries of oligonucleotide and structural analyses.

TABLE 28

Forward primer (SEQ ID NO: 14) designed for mitochondrial 12 S ribosomal RNA region of *Stenobrachius leucopsarus* (SLMB primer 12 S-L) with 5' to 3' end sequences (SENSE) and summaries of oligonucleotide and structural analyses.

DETAILS OF THE INVENTION

This invention of DNA probes developed can be utilized for chromosomal mapping of the myctophid species.

The present invention also contemplates the use of lantern fish primer sets and specific probes in kit form.

Thus in a preferred mode of use, the species specific primers will be employed to conveniently amplify a selected gene region to produce DNA probe directed for use as genetic markers.

The invention would be advantageous for identification of myctophid larvae and hence can facilitate the assessment of water bodies, estimation of genetic resources and genetic variability between myctophid population.

Cyt b probe sequenmces of myctophids will be advantageous to be used for study of comparative human genomics of the genes related to acclimitisation to low oxygen at high altitudes and deep oceanic explorations.

Rod gene probe sequences will be advantageous to be used for study of comparative human genomics of the genes related to acclimitisation to low light like night blindness.

EXAMPLE 1

Chemicals, Reagents, Apparatus Used and Their Sources

| LIST OF CHEMICALS | | |
|---|---|---|
| Name | Company | Catalogue Number |
| 8-Hydroxyquinoline | HIMEDIA | RM1061 |
| Acrylamide 3Xcryst free from DNase, RNase, Protease | SRL | 0144139 |
| Agar powder | HIMEDIA | RM 026 |
| Agarose | SRL | 014011 |
| Agarose | HIMEDIA | RM 187 |
| Benzimidazole (1,3Benzodiazole) Extrapure | SRL | 024727 |
| Bromophenol blue | BDH | 20015 |
| Buffer Tablets pH 7.0 | QUALIGENS | 17301 |
| Butan-1-ol A.R | GLAXO | 12045 |
| Chloroform A.R | S.D.FINE CHEM | 20077 |
| Chloroform for HPLC | SRL | 0322123 |
| E.D.T.A. Disodium salt (Hydroxy Methyl) free from DNase, RNase, protease | HIMEDIA | RM 1195 |
| EDTA | HIMEDIA | RM 678 |
| EDTA Disodium salt L.R | S.D.FINE CHEM | 38025 |
| Ethanol | MERCK | UN 1170 |
| Ethanol (Absolute) | FARCO CHEMICALS | 971109 |
| Ethidium Bromide | HIMEDIA | RM 813 |
| Hydrochloric acid | | |
| Isoamyl alcohol For synthesis | MERCK | 8.18969 |
| Magnesium Chloride A.R | HIMEDIA | RM 728 |
| Methanol Extrapure A.R | SRL | 132977 |
| N,N-Dimethyl Formamide | SRL | 042825 |
| Phenol A.R | RANBAXY | P0130 |
| Potassium Acetate | HIMEDIA | RM 1091 |
| Potassium Chloride Purified | MERCK | 17533 |
| Potassium Dihydrogen Orthophosphate A.R | HIMEDIA | RM 249 |
| Propan-2-ol A.R | QUALIGENS | 73827 |
| Sodium Acetate Anhydrous | HIMEDIA | RM 410 |
| Sodium Chloride A.R | HIMEDIA | RM 853 |
| Sodium dihydrogen Phosphate 2-hydrate Cryst.Pure | MERCK | 17845 |
| Sodium Hydroxide A.R | HIMEDIA | RM 467 |
| Sodium Lauryl Sulphate | HIMEDIA | RM 205 |
| Sodium Nitrite Excela R | QUALIGENS | 15935 |
| Sodium Phosphate dibasic Anhydrous purified | LOBA CHEMIE | 35986 |
| Sucrose From sugar cane A.R | SRL | 194957 |
| Tris Aminomethane (Tris Buffer) | SRL | 2044122 |
| Tris Aminomethane Hydroxy Methyl (Tris buffer) Extrapure A.R | SRL | 204982 |
| Tris buffer A.R | HIMEDIA | RM 262 |
| Tris Hydrochloride | HIMEDIA | RM 613 |
| Tri-Sodium Citrate A.R | HIMEDIA | RM 255 |
| Trypsin 3X Cryst. | SRL | 204013 |
| Trypsin 1:250 | SRL | 2040106 |
| Vitamin $B_{12}$ (Cyanocobalamin) | HIMEDIA | RM184 |
| Yeast Extract powder | SRL | 254011 |

DNA Extractions and Quality and Quantity Check:

Total DNA of *Stenobrachius leucopsarus* was extracted from the muscle tissue by putting in the cocktail of 613.0 μl Lysis Buffer (Lysis Buffer recipe: 10 mM Tris, 400 mM NaCl, 2 mM $Na_2$ EDTA);

30.0 μl 20% SDS (40 g/200 ml water);

7.0 μl Proteinase K (20 μg/μl) which was stored at −20° C. and about 0.1–0.5 grams of the muscle tissue.

Incubated the eppendorf at 55° C. for 12–14 hrs. Added 375 μl of 6 M NaCl and left for 30 min at room temperature.

Centrifuged for 30 min.@14000 rpm. Removed the supernatant and added Chloroform (800 μl) & Centrifuged for 10 min.@12000 rpm. Removed the supernatant and added 1 μl RNAase (10 mg/ml, stored at −20° C.) and kept at 37° C. for 10 min. Added 750 μl volume of isopropanol.

Left the tube at −20° C. for 30 min for DNA precipitation followed by Centrifugation for 30 min.@14000 rpm.

Removed the liquid and dried the pellet under vacuum.

After 1–2 hrs dissolved DNA pellet in 100 μl of sterilized ultrapure water. Stored at 4° C. The DNA extracted was checked for its quality and quantity using UV Spectrophotometer ($OD_{260}$–$OD_{280}$ range of wavelengths of UV. 10.D= 50 μg DNA/ml. 1.80–2.00 range of A1:A2 ratios.

Agarose gel electrophoresis was done to check the molecular weight of DNA.

Agarose gel (0.8%) was prepared in 1× TBE buffer and 2 μl etBr was added to it.

The samples were loaded and 1 Kb DNA Ladder was used as the Marker. The samples were run for 40–45 min. at 72 volts.

The results were viewed in Biorad Gel Doc. 1000.

The computer program used was Molecular analyst.

EXAMPLE 2

The DNA preparation and quality & quantity of *Tarletonbeania crenularis* was done as given in example 1.

EXAMPLE 3

The DNA preparation and quality & quantity of *Protomyctophum crockeri* was done as given in example 2.

EXAMPLE 4

The DNA preparation and quality & quantity of *Lampanyctus regalis* was done as given in example 3.

EXAMPLE 5

The DNA preparation and quality & quantity of *Diaphus theta* was done as given in example 4.

EXAMPLE 6

PCR Amplification Using Forward and Backward D-Loop Primers of *Stenobrachius leucopsarus*

The PCR master mix (100μl) comprised of Taq Buffer $MgCl_2$ free (10.0μl), dNTP all the four nucleotides in the ratio of 1:1:1:1 (08.0µl); D-Loop forward primer 01.0µl with sequences (PRO-L :5' CTA CC 3'), D-Loop backward 01.0µl, with sequences (D-Loop H: 5' CCT GAA GTA GGA ACC AGA TG 3') (SEQ ID NO: 4); MgCl₂ (01.0µl); Taq Polymerase (0.5µl); and ultrapure water (78.2µl).

This master mix was divided into 4 equal parts and put in separate eppendorf tubes. To each tube 0.3 µl of DNA of *Stenobrachius leucopsarus* was added and run for 35 cycles in DNA thermo cycler. (Each cycle consisted of 94 degree C. for 45 Seconds, 48 degree for 45 seconds, and 72 degree C. for 1 minute) and hold at 4 degree Centigrade.

Thermal Cycler used was DNA Thermal Cycler, Perkin Elmer 480.

EXAMPLE 7

As given in example 6, PCR amplification master mix was prepared using forward and backward 12 S RNA primers; 16 S RNA primers, Cyt b primers; ROD, ITS2 primers and DNA 0.3µl of *Stenobrachius leucopsarus* was added individually to all tubes and amplified. The primers used were ROD-F: (SEQ ID NO: 8) 5' CAT ATG AAT ACC CTC AGT ACT ACC 3' and ROD-R: (SEQ ID NO: 7) 5' TCT TTC CGC AGC ACA ACG TGG 3' for Rhodopsin DNA probe; 16SBR-H (SEQ ID NO: 12) 5' CCG GTC TGA ACT CAG ATC ACG T 3' and 16SAR-L (SEQ ID NO: 11) 5' CGC CTG TTT ATC AAA AAC AT 3' 16S for 16 S RNA gene probe; 12SA-L: (SEQ ID NO: 9) 5' AAA CTG GGA TTA GAT ACC CCA CTA T 3' and 12SB-L: (SEQ ID NO: 10) 5' AGA GTG ACG GGC GGT GTG T 3' for 12S RNA gene probe and run for 35 cycles in DNA thermo cycler. (Each cycle consisted of 94 degree C. for 45 Seconds, 48 degree for 45 seconds, and 72 degree C. for 1 minute) and hold at 4 degree Centigrade.

EXAMPLE 8

Cytochrome b DNA probe was amplified by using Cyt 1: (SEQ ID NO: 1) 5' TGA YTT GAA RAA CCA YCG TTG 3' and Cyt 2: (SEQ ID NO: 2) 5' CTC CAR TCT TCG RYT TAC AAG 3' primers followed by reamplification by using CBI-L (SEQ ID NO: 3) 5' CCA TCC AAC ATC TCA GCA TGA TGA AA 3' and Cyt 2: (SEQ ID NO: 2) 5' CTC CAR TCT TCG RYT TAC AAG 3' primers. The DNA template was of *Stenobrachius leucopsarus* and run for 35 cycles in DNA thermo cycler. (Each cycle consisted of 94° C. for 45 Seconds, 48 degree for 45 seconds, and 72 degree C. for 1 minute) and hold at 4 degree Centigrade.

EXAMPLE 9

Similarly, primer ITS1F-ITS2R of Internal transcribed spacers was used for the nested PCR's (ITS1-F: (SEQ ID NO: 41) 5' TTG TAC ACA CCG CCC GTC GC 3' and ITS2-R: (SEQ ID NO: 6) 5' ATA TGC TTA AAT TCA GCG GG 3') and amplified by PCR. Later the ITS2 was reamplified using primers ITS2-F: (SEQ ID NO: 5) 5' CTA CGC CTG TCT GAG TGT C 3' and ITS2-R: (SEQ ID NO: 6) 5' ATA TGC TTA AAT TCA GCG GG 3'. The DNA template was of *Stenobrachius leucopsarus* myctophid fish and run for 35 cycles in DNA thermo cycler. (Each cycle consisted of 94° C. for 45 Seconds, 48° C. for 45 seconds, and 72° C. for 1 minute) and hold at 4 degree Centigrade.

EXAMPLE 10

The PCR amplified and PCR reamplified DNA's were cleaned using QIAquick™ PCR purification Kit which is a product of QIAGEN Inc following their protocols.

EXAMPLE 11

Cycle sequencing was done after following protocols of Perkin Elmer 's ABI PRISM™ Dye terminator Cycle sequencing ready reaction kit with AmpliTaq$^R$ DNA polymerase. Single primer for each gene was used and PCR amplification was done following 25 cycles (each cycle comprised of 96° C. for 30 seconds; Rapid thermal ramp to 46 degree C.; 46° C. for 15 seconds; rapid Thermal ramp to 60 degree C. and 60 degree C. for 4 minutes).

EXAMPLE 12

Purified extension products was done after the same protocol as given on page 8. The DNA pellet was dried under vacuum and stored the dry pellet at –20° C.

EXAMPLE 13

Sequencing on acrylamide gel was done in automated sequencer.

Model 373, DNA sequencing System, Applied Biosystems. A Division of Perkin Elmer. The protocols were used after Sambrook, Fritsch, Maniatis, Molecular Cloning a laboratory manual, second edition, Vol. 2, DNA sequencing 13.47.

40% acrylamide solution was made by acrylamide DNA sequencing grade 380 g; N,N'-methylenebisacrylamide (20 g) and distilled water 600 ml. The TBE buffer (5×) was used. It was made up with Tris Base (54.00 g); Boric acid (27.50 g) Na2 EDTA (4.65 g) and remaining ultra pure autoclaved water to make the volume 1 liter.

EXAMPLE 14

For computation of sequence data program used was "Sequence Navigator, DNA, Applied Systems. A division of Perkin Elmer Corporation". The sequences were sent to Blast email and confirmed by checking for the respective gene segments.

EXAMPLE 15

Ligating the eluted PCR product in to a suitable vector:

Eluted DNA of *Stenobrachius leucopsarus* of cyt b gene was ligated. The total mixture of 20 µl comprised of Water (9 µl); T 4 DNA Ligase Buffer (4 µl); 1 µl Vectors (KS⁻, cut with ECOR V); 5 µl eluted DNA; 1 µl T 4 DNA Ligase.

The vector and the host cells used for cloning was Bluescript KS⁻ phagemid with the ampicillin resistance gene for selection.

Lac Z gene for blue white colony selection. ColE1 origin for replication of phagemid in the absence of helper phage.

F 1(–) origin for recovery of antisense strand of lac Z gene when a host strain containing the bluescript II phagemid.

The host cells used for transformation were *E. coli* blue bacteria (Bacteria Strain XL 1 blue) XL1-Blue: F'::Tn10, pro A⁺B⁺lacI$^q$ (lacZ)M15/recA1endA1gyrA96(Nal$^r$ ) thi hsdR17(r$_k^-$m$_k^+$)supE44relA1 lac.

All these were put in a PCR tube and left for 24 hrs at 4 degree Centigrade cold room for legation. It was labeled as "#SLMB 1, Cytb, DNA Lig."

EXAMPLE 16

Similarly the DNA ligase for genes ROD, ITS2, 12 S RNA and 16 S RNA was prepared.

EXAMPLE 17

Preparation of electro-competent cells for use in electro-transformation.

Prepared 3 liter of LB broth media (10 g Bacto-Tryptone per liter, 5 g Bacto-Yeast per liter and 5 g NaCl per liter) and divided into 4 parts.

From this 2 liters were used for E. coli culture (E. coli strain XL 1 blue was not ampicillin resistant & so no antibiotic was added). It was poured in 4 no. of 1 Liter glass bottles with 500 ml in each.

500 ml was put in a 1 liter bottle to make plates for growing transformed bacteria after electroporation. Prior to autoclaving added only 10 gms of granulated agar (2% agar solution) and later added antibiotic.

250 ml LB was distributed in 20 ml KIMAKAP NO. 73660 tubes@5 ml in each (no antibiotic was added). These tubes were meant for initial growing of electro-competent cells i.e. bacteria.

Last 250 ml was put in a 250 ml glass bottle for use while electroporating to put into the cuvettes.

EXAMPLE 18

Making agar plates to grow transformed bacteria after Electroporation:

After autoclaving the LB broth bottle with 500 ml LB+10 g granulated Agar for bacteriological work was allowed to cool down on the bench to about 50° C. Then added, X gal-500 µl, 500 µl* Ampicillin sodium salt prepared by dissolving 75 mg (0.075 g) in 1.5 ml water, 200 µl * IPTG under sterile conditions. Poured in petridishes. The procedures followed were after Sambrook, Fritsch, Maniatis, Molecular Cloning a laboratory manual, second edition, Vol. 1.

EXAMPLE 19

Electro-transformation of E. coli:

Apparatus used was: E. coli Pulser™

Transformation Apparatus

Bio Rad

Took E. coli and DNA ligase in 0.2 cm cuvettes. Set the E.Coli Pulser apparatus to 2.50 kV and followed the protocols given in Bio Rad catalogue. The white colonies were plated and replated for 3 consective times.

EXAMPLE 20

PCR for confirmation that transformed bacteria has the plasmids with the D-Loop gene inserts.:

PCR amplification using forward and backward D-Loop primers of Stenobrachius leucopsarus.

The PCR master mix (100µl) comprised of Taq Buffer $MgCl_2$ free (10.0µl), dNTP all the four nucleotides in the ratio of 1:1:1:1 (08.0 µl); D-Loop forward primer 01.0µl with sequences (PRO-L: 5' CTA CC 3'), D-Loop backward 01.0 µl, with sequences (D-Loop H: 5' CCT GAA GTA GGA ACC AGA TG 3') (SEQ ID NO: 4); $MgCl_2$ (01.0µl); Taq Polymerase (0.5µl); and ultrapure water (78.2µl).

This plaster mix was divided into 4 equal parts and put in separate eppendorf tubes. To each tube DNA was added by getting a pick from the replated last set of white colonies and run for 35 cycles in DNA thermo cycler. (Each cycle consisted of 94° C. for 45 Seconds, 48 degree for 45 seconds, and 72° C. for 1 minute) and hold at 4 degree Centigrade.

Thermal Cycler used was: DNA Thermal Cycler, Perkin Elmer 480.

EXAMPLE 21

Similarly using DNA from the colonies did PCR for gene Cytb, ITS2, 12 S RNA and 16 S RNA by using the respective primers as mentioned above in example 6–9. The amplified DNA was checked on the gel with the 1 Kb DNA marker and checked for the size of the insert.

EXAMPLE 22

The colonies showing the brightest band for the particular gene insert were inoculated in LB broth under sterile conditions with flame, added 5 µl of Ampicillin and grown at 37 degree Centigrade.

EXAMPLE 23

Plasmid DNA purification was followed from Wizard™ minipreps DNA Purification system Technical bulletin, revised 1/94part #TB 117 and cloned gene probes were thus developed for D-Loop, ITS2, Cyt b, 12 S and 16 s of Stenobrachius leucosparus myctophid fish.

EXAMPLE 24

Checking Purity and Specificity of the Probe

The plasmid with insert was first cut with ECOR I restriction enzyme and following were added in a PCR tube (1 µl DNA (plasmid), 2 µl ECOR Buffer, 1 µl ECOR Enzyme, 16 µl MQ water to make the volume 20 µl).

Run at 0.7% agarose gel on 72 volts with 1 kb DNA ladder. And keeping negative control of plasmids from the blue colonies. The band shown will be of the size of plasmid+gene. In this case the 12 S gene is 411 bp and plasmid is 3000 bp. So the position of the band was between the 3054 and 4072 bp bands. The DNA probe of 12 S with us is the pure cloned gene from myctophid Stenobrachius leucopsarus.

EXAMPLE 25

Similarly we have developed pure DNA probes of the gene segment from 16 S RNA, D-Loop, Cytb, and ITS2 genes.

EXAMPLE 26

Sequencing of probe:

Once the Species specific probe was ready it was sequenced to see the sequences to ascertain that these were the same sequences that we started with. The steps of example 6–14 were followed in the same manner. Only the DNA template is of the probes from example 23.

EXAMPLE 27

The blast operation was performed by sending pasta format of all the gene sequences to the Blast@ NCBI and asking for related sequences. The results confirmed that the genes probed belonged to the Cytb, D-Loop, Rod and ITS2, 12 S rRNA and 16 S rRNA genes.

EXAMPLE 28

The species specific primers of cyt b, D-Loop, ROD, ITS2, 12S rRNA and 16S rRNA gene regions of the myctophid Stenobrachius leucopsarus (SLMB) and 12S rRNA and 16S rRNA gene regions of four more myctophids like

*Lampanyctus regalis, Diaphus theta; Tarletonbeania crenularis* & *Protomyctophum crockeri* are designed using the "Generunner".

EXAMPLE 29

The sequences of the species specific primers of cyt b, D-Loop, ROD, ITS2, 12S rRNA and 16S rRNA gene regions of the myctophid *Stenobrachius leucopsarus* (SLMB) and 12S rRNA and 16S rRNA gene regions of four more myctophids like *Lampanyctus regalis, Diaphus theta; Tarletonbeania crenularis* & *Protomyctophum crockeri* are designed using the "Generunner" program for the first time.

EXAMPLE 30

Both the Forward (also written as "L" and "Sense") and Backward primers (also written as "H" and "Antisense") sequences for all the above said gene regions for all the species are designed.

EXAMPLE 31

All the primers designed had no Hairpin Loops, Dimers, Bulge Loops and Internal Loops. There are no palindromes.

Analysis of "table1 (slmb primer cyt L)" a 20-mer DNA Oligonucleotide (Sense)
5' CAA CCT CAT CTG TCG TAA AC 3'

| Oligonucleotide Analysis | | Analysis Parameters | | |
|---|---|---|---|---|
| Molecular weight | 6101.0 | | Delta G Temperature | 25.0 degrees C. |
| Tm thermodynamic | 56.4 | degrees C. | Probe concentration | 0.6 pMol |
| Filter Tm | 48.8 | degrees C. | Salt concentration | 1000.0 mMol |
| % GC Tm | 66.2 | degrees C. | Formamide concentration | 0.0% |
| AT + GC Tm | 58.0 | degrees C. | 3' End length | 7 bases |
| Absorbance | 5.3 | nMol/A260 | Run length | 4 bases |
| Absorbance | 32.5 | ug/A260 | Palindrome length | 8 bases |
| Percent GC | 45.0% | | Hairpin loop stem length | 3 bases |
| Delta G | −28.7 | kCal/Mol | | |
| Delta H | −140.6 | kCal/Mol | | |
| Delta S | −368.0 | eu | | |
| 3' End Delta G | −5.9 | kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 2 (slmb primer cyt H)" a 20-mer DNA Oligonucleotide (Antisense)
5' GCT CGG GCT GCT GGA ATC TT 3'

| Oligonucleotide Analysis | | Analysis Parameters | | |
|---|---|---|---|---|
| Molecular weight | 6220.1 | | Delta G Temperature | 25.0 degrees C. |
| Tm thermodynamic | 70.8 | degrees C. | Probe concentration | 0.6 pMol |
| Filter Tm | 63.2 | degrees C. | Salt concentration | 1000.0 mMol |
| % GC Tm | 72.3 | degrees C. | Formamide concentration | 0.0% |
| AT + GC Tm | 64.0 | degrees C. | 3' End length | 7 bases |
| Absorbance | 5.6 | nMol/A260 | Run length | 4 bases |
| Absorbance | 34.8 | ug/A260 | Palindrome length | 8 bases |
| Percent GC | 60.0% | | Hairpin loop stem length | 3 bases |
| Delta G | −37.5 | kCal/Mol | | |
| Delta H | −164.6 | kCal/Mol | | |
| Delta S | −419.9 | eu | | |
| 3' End Delta G | −5.1 | kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 3 (slmb primer ITS2 F)" a 20-mer DNA Oligonucleotide (Sense)
5' ACT TGA CTG ACC TTC TTA CT 3'

| Oligonucleotide Analysis | | Analysis Parameters | |
|---|---|---|---|
| Molecular weight | 6098.0 | Delta G Temperature | 25.0 degrees C. |
| Tm thermodynamic | 51.3 degrees C. | Probe concentration | 0.6 pMol |
| Filter Tm | 43.7 degrees C. | Salt concentration | 1000.0 mMol |
| % GC Tm | 64.2 degrees C. | Formamide concentration | 0.0% |
| AT + GC Tm | 56.0 degrees C. | 3' End length | 7 bases |
| Absorbance | 5.6 nMol/A260 | Run length | 4 bases |
| Absorbance | 34.0 ug/A260 | Palindrome length | 8 bases |
| Percent GC | 40.0% | Hairpin loop stem length | 3 bases |
| Delta G | −26.5 kCal/Mol | | |
| Delta H | −137.7 kCal/Mol | | |
| Delta S | −365.8 eu | | |
| 3' End Delta G | −3.9 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 4 (slmb primer ITS2-H)" a 24-mer DNA Oligonucleotide (Antisense)
5' ATA CTC TGC GGA CAT ACT TGA CTG 3'

| Oligonucleotide Analysis | | Analysis Parameters | |
|---|---|---|---|
| Molecular weight | 7407.9 | Delta G Temperature | 25.0 degrees C. |
| Tm thermodynamic | 65.4 degrees C. | Probe concentration | 0.6 pMol |
| Filter Tm | 57.8 degrees C. | Salt concentration | 1000.0 mMol |
| % GC Tm | 72.2 degrees C. | Formamide concentration | 0.0% |
| AT + GC Tm | 70.0 degrees C. | 3' End length | 7 bases |
| Absorbance | 4.4 nMol/A260 | Run length | 4 bases |
| Absorbance | 32.4 ug/A260 | Palindrome length | 8 bases |
| Percent GC | 45.8% | Hairpin loop stem length | 3 bases |
| Delta G | −35.5 kCal/Mol | | |
| Delta H | −169.5 kCal/Mol | | |
| Delta S | −442.0 eu | | |
| 3' End Delta G | −5.2 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 5 (slmb primer pro-L)" a 24-mer DNA Oligonucleotide (Sense)
5' CAG TCT CGT CAA ACC AAG TCA AAC 3'

| Oligonucleotide Analysis | | Analysis Parameters | |
|---|---|---|---|
| Molecular weight | 7354.9 | Delta G Temperature | 25.0 degrees C. |
| Tm thermodynamic | 67.8 degrees C. | Probe concentration | 0.6 pMol |
| Filter Tm | 60.2 degrees C. | Salt concentration | 1000.0 mMol |
| % GC Tm | 72.2 degrees C. | Formamide concentration | 0.0% |
| AT + GC Tm | 70.0 degrees C. | 3' End length | 7 bases |
| Absorbance | 4.3 nMol/A260 | Run length | 4 bases |
| Absorbance | 31.4 ug/A260 | Palindrome length | 8 bases |
| Percent GC | 45.8% | Hairpin loop stem length | 3 bases |
| Delta G | −36.5 kCal/Mol | | |
| Delta H | −169.9 kCal/Mol | | |
| Delta S | −439.7 eu | | |
| 3' End Delta G | −4.9 kCal/Mol | | |

Analysis of "table 5 (slmb primer pro-L)" a 24-mer DNA Oligonucleotide (Sense)
5' CAG TCT CGT CAA ACC AAG TCA AAC 3'

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 6 (slmb primer Dloop-H)" a 23-mer DNA Oligonucleotide (Antisense)
5' ATA ATC ATC CAG CAT AAA CAC AC 3'

| Oligonucleotide Analysis | | Analysis Parameters | |
|---|---|---|---|
| Molecular weight | 7033.7 | Delta G Temperature | 25.0 degrees C. |
| Tm thermodynamic | 61.2 degrees C. | Probe concentration | 0.6 pMol |
| Filter Tm | 53.6 degrees C. | Salt concentration | 1000.0 mMol |
| % GC Tm | 66.4 degrees C. | Formamide concentration | 0.0% |
| AT + GC Tm | 62.0 degrees C. | 3' End length | 7 bases |
| Absorbance | 4.3 nMol/A260 | Run length | 4 bases |
| Absorbance | 30.0 ug/A260 | Palindrome length | 8 bases |
| Percent GC | 34.8% | Hairpin loop stem length | 3 bases |
| Delta G | −32.9 kCal/Mol | | |
| Delta H | −163.3 kCal/Mol | | |
| Delta S | −429.7 eu | | |
| 3' End Delta G | −4.6 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 7 (slmb primer ROD-L)" a 20-mer DNA Oligonucleotide (Sense)
5' CCT GGT AGA GTT CGC CGT CA 3'

| Oligonucleotide Analysis | | Analysis Parameters | |
|---|---|---|---|
| Molecular weight | 6189.0 | Delta G Temperature | 25.0 degrees C. |
| Tm thermodynamic | 67.4 degrees C. | Probe concentration | 0.6 pMol |
| Filter Tm | 59.8 degrees C. | Salt concentration | 1000.0 mMol |
| % GC Tm | 72.3 degrees C. | Formamide concentration | 0.0% |
| AT + GC Tm | 64.0 degrees C. | 3' End length | 7 bases |
| Absorbance | 5.3 nMol/A260 | Run length | 4 bases |
| Absorbance | 33.0 ug/A260 | Palindrome length | 8 bases |
| Percent GC | 60.0% | Hairpin loop stem length | 3 bases |
| Delta G | −34.7 kCal/Mol | | |
| Delta H | −154.3 kCal/Mol | | |
| Delta S | −154.4 eu | | |
| 3' End Delta G | −9.6 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 8 (slmb primer ROD-H)" a 22-mer DNA Oligonucleotide (Antisense)
5' CGT GTT CCT TAT CAT TGT GCC T 3'

| Oligonucleotide Analysis | | Analysis Parameters | |
|---|---|---|---|
| Molecular weight | 6738.4 | Delta G Temperature | 25.0 degrees C. |
| Tm thermodynamic | 66.4 degrees C. | Probe concentration | 0.6 pMol |
| Filter Tm | 58.8 degrees C. | Salt concentration | 1000.0 mMol |
| % GC Tm | 69.5 degrees C. | Formamide concentration | 0.0% |
| AT + GC Tm | 64.0 degrees C. | 3' End length | 7 bases |
| Absorbance | 5.2 nMol/A260 | Run length | 4 bases |
| Absorbance | 34.9 ug/A260 | Palindrome length | 8 bases |
| Percent GC | 45.5% | Hairpin loop stem length | 3 bases |
| Delta G | −35.4 kCal/Mol | | |
| Delta H | −165.0 kCal/Mol | | |
| Delta S | −427.3 eu | | |
| 3' End Delta G | −7.9 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 9 (LRMB primer 16S-L)" a 21-mer DNA Oligonucleotide (Sense)
5' CAC CAG CCA AGT ATG TTT CTC 3'

| Oligonucleotide Analysis | | Analysis Parameters | |
|---|---|---|---|
| Molecular weight | 6421.2 | Delta G Temperature | 25.0 degrees C. |
| Tm thermodynamic | 61.5 degrees C. | Probe concentration | 0.6 pMol |
| Filter Tm | 53.9 degrees C. | Salt concentration | 1000.0 mMol |
| % GC Tm | 68.9 degrees C. | Formamide concentration | 0.0% |
| AT + GC Tm | 62.0 degrees C. | 3' End length | 7 bases |
| Absorbance | 5.1 nMol/A260 | Run length | 4 bases |
| Absorbance | 33.0 ug/A260 | Palindrome length | 8 bases |
| Percent GC | 47.6% | Hairpin loop stem length | 3 bases |
| Delta G | −31.9 kCal/Mol | | |
| Delta H | −152.3 kCal/Mol | | |
| Delta S | −396.4 eu | | |
| 3' End Delta G | −4.9 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 10 (LRMB primer 16S-H)" a 18-mer DNA Oligonucleotide (Antisense)
5' TCG TAG TTC AGC AGT CAG 3'

| Oligonucleotide Analysis | | Analysis Parameters | |
|---|---|---|---|
| Molecular weight | 5594.7 | Delta G Temperature | 25.0 degrees C. |
| Tm thermodynamic | 51.2 degrees C. | Probe concentration | 0.6 pMol |
| Filter Tm | 43.6 degrees C. | Salt concentration | 1000.0 mMol |
| % GC Tm | 64.5 degrees C. | Formamide concentration | 0.0% |
| AT + GC Tm | 54.0 degrees C. | 3' End length | 7 bases |
| Absorbance | 5.7 nMol/A260 | Run length | 4 bases |
| Absorbance | 31.8 ug/A260 | Palindrome length | 8 bases |
| Percent GC | 50.0% | Hairpin loop stem length | 3 bases |
| Delta G | −25.3 kCal/Mol | | |
| Delta H | −123.0 kCal/Mol | | |
| Delta S | −320.5 eu | | |
| 3' End Delta G | −4.9 kCal/Mol | | |

Analysis of "table 10 (LRMB primer 16S-H)" a 18-mer DNA Oligonucleotide (Antisense)
5' TCG TAG TTC AGC AGT CAG 3'

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 11 (LRMB primer 12S-L)" a 19-mer DNA Oligonucleotide (Sense)
5' CTA TTC GCC TCG CTC AGA C 3'

| Oligonucleotide Analysis | | Analysis Parameters | |
|---|---|---|---|
| Molecular weight | 5779.8 | Delta G Temperature | 25.0 degrees C. |
| Tm thermodynamic | 62.1 degrees C. | Probe concentration | 0.6 pMol |
| Filter Tm | 54.5 degrees C. | Salt concentration | 1000.0 mMol |
| % GC Tm | 69.7 degrees C. | Formamide concentration | 0.0% |
| AT + GC Tm | 60.0 degrees C. | 3' End length | 7 bases |
| Absorbance | 6.0 nMol/A260 | Run length | 4 bases |
| Absorbance | 34.6 ug/A260 | Palindrome length | 8 bases |
| Percent GC | 57.9% | Hairpin loop stem length | 3 bases |
| Delta G | −31.8 kCal/Mol | | |
| Delta H | −146.6 kCal/Mol | | |
| Delta S | −378.6 eu | | |
| 3' End Delta G | −4.6 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 12 (LRMB primer 12S-H)" a 23-mer DNA Oligonucleotide (Antisense)
5' GCC TCC ATC ATC CCT CAC CTT AC 3'

| Oligonucleotide Analysis | | Analysis Parameters | |
|---|---|---|---|
| Molecular weight | 6895.5 | Delta G Temperature | 25.0 degrees C. |
| Tm thermodynamic | 70.8 degrees C. | Probe concentration | 0.6 pMol |
| Filter Tm | 63.2 degrees C. | Salt concentration | 1000.0 mMol |
| % GC Tm | 75.3 degrees C. | Formamide concentration | 0.0% |
| AT + GC Tm | 72.0 degrees C. | 3' End length | 7 bases |
| Absorbance | 5.1 nMol/A260 | Run length | 4 bases |
| Absorbance | 34.9 ug/A260 | Palindrome length | 8 bases |
| Percent GC | 56.5% | Hairpin loop stem length | 3 bases |
| Delta G | −38.9 kCal/Mol | | |
| Delta H | −174.6 kCal/Mol | | |
| Delta S | −448.9 eu | | |
| 3' End Delta G | −5.1 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 13 (DTMB primer 16S-H)" a 20-mer DNA Oligonucleotide (Antisense)
5' CTC CGT CCG TCT CGC CTC TG 3'

| Oligonucleotide Analysis | | Analysis Parameters | |
| --- | --- | --- | --- |
| Molecular weight | 6052.0 | Delta G Temperature | 25.0 degrees C. |
| Tm thermodynamic | 71.7 degrees C. | Probe concentration | 0.6 pMol |
| Filter Tm | 64.1 degrees C. | Salt concentration | 1000.0 mMol |
| % GC Tm | 76.4 degrees C. | Formamide concentration | 0.0% |
| AT + GC Tm | 68.0 degrees C. | 3' End length | 7 bases |
| Absorbance | 6.1 nMol/A260 | Run length | 4 bases |
| Absorbance | 37.2 ug/A260 | Palindrome length | 8 bases |
| Percent GC | 70.0% | Hairpin loop stem length | 3 bases |
| Delta G | −37.1 kCal/Mol | | |
| Delta H | −157.8 kCal/Mol | | |
| Delta S | −398.9 eu | | |
| 3' End Delta G | −7.9 kCal/Mol | | |

Structural Analysis Summary

| | |
| --- | --- |
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 14 (DTMB primer 16S-L)" a 22-mer DNA Oligonucleotide (Sense)
5' AAA TCC GCC CTT ATG TGT GTT C 3'

| Oligonucleotide Analysis | | Analysis Parameters | |
| --- | --- | --- | --- |
| Molecular weight | 6756.4 | Delta G Temperature | 25.0 degrees C. |
| Tm thermodynamic | 67.9 degrees C. | Probe concentration | 0.6 pMol |
| Filter Tm | 60.3 degrees C. | Salt concentration | 1000.0 mMol |
| % GC Tm | 69.5 degrees C. | Formamide concentration | 0.0% |
| AT + GC Tm | 64.0 degrees C. | 3' End length | 7 bases |
| Absorbance | 4.9 nMol/A260 | Run length | 4 bases |
| Absorbance | 33.3 ug/A260 | Palindrome length | 8 bases |
| Percent GC | 45.5% | Hairpin loop stem length | 3 bases |
| Delta G | −36.9 kCal/Mol | | |
| Delta H | −171.5 kCal/Mol | | |
| Delta S | −444.2 eu | | |
| 3' End Delta G | −4.9 kCal/Mol | | |

Structural Analysis Summary

| | |
| --- | --- |
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 15 (DTMB primer 12S-H)" a 22-mer DNA Oligonucleotide (Antisense)
5' CAT CGG CTT GCT CTA TTC CTT G 3'

| Oligonucleotide Analysis | | Analysis Parameters | |
| --- | --- | --- | --- |
| Molecular weight | 6723.4 | Delta G Temperature | 25.0 degrees C. |
| Tm thermodynamic | 68.8 degrees C. | Probe concentration | 0.6 pMol |
| Filter Tm | 61.2 degrees C. | Salt concentration | 1000.0 mMol |
| % GC Tm | 71.3 degrees C. | Formamide concentration | 0.0% |
| AT + GC Tm | 66.0 degrees C. | 3' End length | 7 bases |
| Absorbance | 5.3 nMol/A260 | Run length | 4 bases |
| Absorbance | 35.5 ug/A260 | Palindrome length | 8 bases |
| Percent GC | 50.0% | Hairpin loop stem length | 3 bases |
| Delta G | −37.5 kCal/Mol | | |
| Delta H | −172.0 kCal/Mol | | |
| Delta S | −444.3 eu | | |
| 3' End Delta G | −7.0 kCal/Mol | | |

-continued

Analysis of "table 15 (DTMB primer 12S-H)" a 22-mer DNA Oligonucleotide (Antisense)
5' CAT CGG CTT GCT CTA TTC CTT G 3'

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 16 (DTMB primer 12S-L)" a 19-mer DNA Oligonucleotide (Sense)
5' TCT ATC GGC GGC GTA TCA C 3'

| Oligonucleotide Analysis | | Analysis Parameters | |
|---|---|---|---|
| Molecular weight | 5859.8 | Delta G Temperature | 25.0 degrees C. |
| Tm thermodynamic | 65.8 degrees C. | Probe concentration | 0.6 pMol |
| Filter Tm | 58.2 degrees C. | Salt concentration | 1000.0 mMol |
| % GC Tm | 69.7 degrees C. | Formamide concentration | 0.0% |
| AT + GC Tm | 60.0 degrees C. | 3' End length | 7 bases |
| Absorbance | 5.7 nMol/A260 | Run length | 4 bases |
| Absorbance | 33.4 ug/A260 | Palindrome length | 8 bases |
| Percent GC | 57.9% | Hairpin loop stem length | 3 bases |
| Delta G | −33.9 kCal/Mol | | |
| Delta H | −152.5 kCal/Mol | | |
| Delta S | −391.2 eu | | |
| 3' End Delta G | −3.5 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 17 (TCMB primer 16S-H)" a 21-mer DNA Oligonucleotide (Antisense)
5' GGC GAT TCT ACG GCA CGG GCG 3'

| Oligonucleotide Analysis | | Analysis Parameters | |
|---|---|---|---|
| Molecular weight | 6568.3 | Delta G Temperature | 25.0 degrees C. |
| Tm thermodynamic | 80.4 degrees C. | Probe concentration | 0.6 pMol |
| Filter Tm | 72.8 degrees C. | Salt concentration | 1000.0 mMol |
| % GC Tm | 78.6 degrees C. | Formamide concentration | 0.0% |
| AT + GC Tm | 72.0 degrees C. | 3' End length | 7 bases |
| Absorbance | 5.1 nMol/A260 | Run length | 4 bases |
| Absorbance | 33.3 ug/A260 | Palindrome length | 8 bases |
| Percent GC | 71.4% | Hairpin loop stem length | 3 bases |
| Delta G | −44.7 kCal/Mol | | |
| Delta H | −186.4 kCal/Mol | | |
| Delta S | −468.6 eu | | |
| 3' End Delta G | −12.8 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 18 (TCMB primer 16S-L)" a 22-mer DNA Oligonucleotide (Antisense)
5' AAA CTG GTC CTC AAC TAT GTC A 3'

| Oligonucleotide Analysis | | Analysis Parameters | |
|---|---|---|---|
| Molecular weight | 6758.5 | Delta G Temperature | 25.0 degrees C. |
| Tm thermodynamic | 60.7 degrees C. | Probe concentration | 0.6 pMol |
| Filter Tm | 53.1 degrees C. | Salt concentration | 1000.0 mMol |
| % GC Tm | 67.6 degrees C. | Formamide concentration | 0.0% |
| AT + GC Tm | 62.0 degrees C. | 3' End length | 7 bases |
| Absorbance | 4.7 nMol/A260 | Run length | 4 bases |
| Absorbance | 31.7 ug/A260 | Palindrome length | 8 bases |
| Percent GC | 40.9% | Hairpin loop stem length | 3 bases |
| Delta G | −31.7 kCal/Mol | | |
| Delta H | −153.3 kCal/Mol | | |
| Delta S | −400.5 eu | | |
| 3' End Delta G | −4.1 kCal/Mol | | |

| Structural Analysis Summary | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 19 (TCMB primer 12S-H)" a 22-mer DNA Oligonucleotide (Antisense)
5' CCG ATT CAG CCA CGA TTC CCT C 3'

| Oligonucleotide Analysis | | Analysis Parameters | |
|---|---|---|---|
| Molecular weight | 6671.4 | Delta G Temperature | 25.0 degrees C. |
| Tm thermodynamic | 74.6 degrees C. | Probe concentration | 0.6 pMol |
| Filter Tm | 67.0 degrees C. | Salt concentration | 1000.0 nMol |
| % GC Tm | 75.0 degrees C. | Formamide concentration | 0.0% |
| AT + GC Tm | 70.0 degrees C. | 3' End length | 7 bases |
| Absorbance | 5.1 nMol/A260 | Run length | 4 bases |
| Absorbance | 34.2 ug/A260 | Palindrome length | 8 bases |
| Percent GC | 59.1% | Hairpin loop stem length | 3 bases |
| Delta G | −40.8 kCal/Mol | | |
| Delta H | −176.0 kCal/Mol | | |
| Delta S | −447.5 eu | | |
| 3' End Delta G | −7.9 kCal/Mol | | |

| Structural Analysis Summary | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 20 (TCMB primer 12S-L)" a 21-mer DNA Oligonucleotide (Sense)
5' CCT AAA GCC CAG ATA ACT ACA 3'

| Oligonucleotide Analysis | | Analysis Parameters | |
|---|---|---|---|
| Molecular weight | 6432.3 | Delta G Temperature | 25.0 degrees C. |
| Tm thermodynamic | 59.2 degrees C. | Probe concentration | 0.6 pMol |
| Filter Tm | 51.6 degrees C. | Salt concentration | 1000.0 mMol |
| % GC Tm | 66.9 degrees C. | Formamide concentration | 0.0% |
| AT + GC Tm | 60.0 degrees C. | 3' End length | 7 bases |
| Absorbance | 4.8 nMol/A260 | Run length | 4 bases |
| Absorbance | 30.6 ug/A260 | Palindrome length | 8 bases |
| Percent GC | 42.9% | Hairpin loop stem length | 3 bases |
| Delta G | −31.7 kCal/Mol | | |
| Delta H | −159.4 kCal/Mol | | |
| Delta S | −421.0 eu | | |
| 3' End Delta G | −3.9 kCal/Mol | | |

Analysis of "table 20 (TCMB primer 12S-L)" a 21-mer DNA Oligonucleotide (Sense)
5' CCT AAA GCC CAG ATA ACT ACA 3'

| Structural Analysis Summary | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 21 (PCMB primer 16S-H)" a 22-mer DNA Oligonucleotide (Antisense)
5' CGT GTT CTG ATG ATG ATG TGC T 3'

| Oligonucleotide Analysis | | | Analysis Parameters | | |
|---|---|---|---|---|---|
| Molecular weight | 6867.5 | | Delta G Temperature | 25.0 | degrees |
| Tm thermodynamic | 64.7 | degrees C. | Probe concentration | 0.6 | pMol |
| Filter Tm | 57.1 | degrees C. | Salt concentration | 1000.0 | mMol |
| % GC Tm | 69.5 | degrees C. | Formamide concentration | 0.0% | |
| AT + GC Tm | 64.0 | degrees C. | 3' End length | 7 | bases |
| Absorbance | 4.9 | nMol/A260 | Run length | 4 | bases |
| Absorbance | 33.4 | ug/A260 | Palindrome length | 8 | bases |
| Percent GC | 45.5% | | Hairpin loop stem length | 3 | bases |
| Delta G | −33.0 | kCal/Mol | | | |
| Delta H | −150.2 | kCal/Mol | | | |
| Delta S | −385.9 | eu | | | |
| 3' End Delta G | −6.3 | kCal/Mol | | | |

| Structural Analysis Summary | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 22 (PCMB primer 16S-L)" a 19-mer DNA Oligonucleotide (Sense)
5' ATT CCT TCC TCT TAG TAT G 3'

| Oligonucleotide Analysis | | | Analysis Parameters | | |
|---|---|---|---|---|---|
| Molecular weight | 5799.8 | | Delta G Temperature | 25.0 | degrees C. |
| Tm thermodynamic | 49.5 | degrees C. | Probe concentration | 0.6 | pMol |
| Filter Tm | 41.9 | degrees C. | Salt concentration | 1000.0 | mMol |
| % GC Tm | 61.1 | degrees C. | Formamide concentration | 0.0% | |
| AT + GC Tm | 52.0 | degrees C. | 3' End length | 7 | bases |
| Absorbance | 5.8 | nMol/A260 | Run length | 4 | bases |
| Absorbance | 33.6 | ug/A260 | Palindrome length | 8 | bases |
| Percent GC | 36.8% | | Hairpin loop stem length | 3 | bases |
| Delta G | −26.1 | kCal/Mol | | | |
| Delta H | −138.8 | kCal/Mol | | | |
| Delta S | −371.5 | eu | | | |
| 3' End Delta G | −3.1 | kCal/Mol | | | |

| Structural Analysis Summary | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 23 (PCMB primer 12S-H)" a 22-mer DNA Oligonucleotide (Antisense)
5' GCT GAA CTT ACT ATG CCC TAC T 3'

| Oligonucleotide Analysis | | Analysis Parameters | |
|---|---|---|---|
| Molecular weight | 6725.4 | Delta G Temperature | 25.0 degrees C. |
| Tm thermodynamic | 60.3 degrees C. | Probe concentration | 0.6 pMol |
| Filter Tm | 52.7 degrees C. | Salt concentration | 1000.0 mMol |
| % GC Tm | 69.5 degrees C. | Formamide concentration | 0.0% |
| AT + GC Tm | 64.0 degrees C. | 3' End length | 7 bases |
| Absorbance | 5.0 nMol/A260 | Run length | 4 bases |
| Absorbance | 33.6 ug/A260 | Palindrome length | 8 bases |
| Percent GC | 46.5% | Hairpin loop stem length | 3 bases |
| Delta G | −32.7 kCal/Mol | | |
| Delta H | −164.7 kCal/Mol | | |
| Delta S | −435.2 eu | | |
| 3' End Delta G | −6.6 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 24 (PCMB primer 12S-L)" a 20-mer DNA Oligonucleotide (Sense)
5' CCG ATT GAC GCC GAA CTA TG 3'

| Oligonucleotide Analysis | | Analysis Parameters | |
|---|---|---|---|
| Molecular weight | 6182.1 | Delta G Temperature | 25.0 degrees C. |
| Tm thermodynamic | 68.1 degrees C. | Probe concentration | 0.6 pMol |
| Filter Tm | 60.5 degrees C. | Salt concentration | 1000.0 mMol |
| % GC Tm | 70.3 degrees C. | Formamide concentration | 0.0% |
| AT + GC Tm | 62.0 degrees C. | 3' End length | 7 bases |
| Absorbance | 5.3 nMol/A260 | Run length | 4 bases |
| Absorbance | 32.5 ug/A260 | Palindrome length | 8 bases |
| Percent GC | 55.0% | Hairpin loop stem length | 3 bases |
| Delta G | −35.6 kCal/Mol | | |
| Delta H | −159.4 kCal/Mol | | |
| Delta S | −408.5 eu | | |
| 3' End Delta G | −4.1 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 25 (SLMB primer 16S-H)" a 18-mer DNA Oligonucleotide (Antisense)
5' TAC GCA TAA CGG CTC TGG 3'

| Oligonucleotide Analysis | | Analysis Parameters | |
|---|---|---|---|
| Molecular weight | 5579.7 | Delta G Temperature | 25.0 degrees C. |
| Tm thermodynamic | 61.4 degrees C. | Probe concentration | 0.6 pMol |
| Filter Tm | 53.8 degrees C. | Salt concentration | 1000.0 mMol |
| % GC Tm | 66.8 degrees C. | Formamide concentration | 0.0% |
| AT + GC Tm | 56.0 degrees C. | 3' End length | 7 bases |
| Absorbance | 5.9 nMol/A260 | Run length | 4 bases |
| Absorbance | 32.8 ug/A260 | Palindrome length | 8 bases |
| Percent GC | 55.6% | Hairpin loop stem length | 3 bases |
| Delta G | −31.0 kCal/Mol | | |
| Delta H | −143.5 kCal/Mol | | |
| Delta S | −370.2 eu | | |
| 3' End Delta G | −7.9 kCal/Mol | | |

Analysis of "table 25 (SLMB primer 16S-H)" a 18-mer DNA Oligonucleotide (Antisense)
5' TAC GCA TAA CGG CTC TGG 3'

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 26 (SLMB primer 16S-L)" a 22-mer DNA Oligonucleotide (Sense)
5' CTA CTA CAC CTC AAC TAC ATC T 3'

| Oligonucleotide Analysis | | Analysis Parameters | |
|---|---|---|---|
| Molecular weight | 6638.4 | Delta G Temperature | 25.0 degrees C. |
| Tm thermodynamic | 52.4 degrees C. | Probe concentration | 0.6 pMol |
| Filter Tm | 44.8 degrees C. | Salt concentration | 1000.0 mMol |
| % GC Tm | 67.6 degrees C. | Formamide concentration | 0.0% |
| AT + GC Tm | 62.0 degrees C. | 3' End length | 7 bases |
| Absorbance | 4.9 nMol/A260 | Run length | 4 bases |
| Absorbance | 32.8 ug/A260 | Palindrome length | 8 bases |
| Percent GC | 40.9% | Hairpin loop stem length | 3 bases |
| Delta G | −27.6 kCal/Mol | | |
| Delta H | −146.8 kCal/Mol | | |
| Delta S | −392.2 eu | | |
| 3' End Delta G | −3.8 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 27 (SLMB primer 12S-H)" a 19-mer DNA Oligonucleotide (Antisense)
5' CCC ACT CAC TGC TAA CTC C 3'

| Oligonucleotide Analysis | | Analysis Parameters | |
|---|---|---|---|
| Molecular weight | 5708.8 | Delta G Temperature | 25.0 degrees C. |
| Tm thermodynamic | 58.4 degrees C. | Probe concentration | 0.6 pMol |
| Filter Tm | 50.8 degrees C. | Salt concentration | 1000.0 mMol |
| % GC Tm | 69.7 degrees C. | Formamide concentration | 0.0% |
| AT + GC Tm | 60.0 degrees C. | 3' End length | 7 bases |
| Absorbance | 6.1 nMol/A260 | Run length | 4 bases |
| Absorbance | 35.0 ug/A260 | Palindrome length | 8 bases |
| Percent GC | 57.9% | Hairpin loop stem length | 3 bases |
| Delta G | −29.4 kCal/Mol | | |
| Delta H | −138.5 kCal/Mol | | |
| Delta S | −359.0 eu | | |
| 3' End Delta G | −5.4 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

Analysis of "table 28 (SLMB primer 12S-L)" a 21-mer DNA Oligonucleotide (Sense)
5' GGC TAA CTA CAA TCA TCT GCT 3'

| Oligonucleotide Analysis | | Analysis Parameters | |
|---|---|---|---|
| Molecular weight | 6445.2 | Delta G Temperature | 25.0 degrees C. |
| Tm thermodynamic | 58.5 degrees C. | Probe concentration | 0.6 pMol |
| Filter Tm | 50.9 degrees C. | Salt concentration | 1000.0 mMol |
| % GC Tm | 66.9 degrees C. | Formamide concentration | 0.0% |
| AT + GC Tm | 60.0 degrees C. | 3' End length | 7 bases |
| Absorbance | 5.1 nMol/A260 | Run length | 4 bases |
| Absorbance | 32.6 ug/A260 | Palindrome length | 8 bases |
| Percent GC | 42.9% | Hairpin loop stem length | 3 bases |
| Delta G | −30.8 kCal/Mol | | |
| Delta H | −153.4 kCal/Mol | | |
| Delta S | −403.9 eu | | |
| 3' End Delta G | −6.3 kCal/Mol | | |

Structural Analysis Summary

| | |
|---|---|
| Number of base runs/palindromes | 0/0 |
| Number of hairpin loops | 0 |
| Number of dimers/2-oligo dimers | 0/0 |
| Number of bulge loops/2-oligo bulges | 0/0 |
| Number of internal loops/2-oligo internals | 0/0 |

SEQUENCE LISTING

<160> NUMBER OF SEQ IDS NOS: 45

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 1
tgayttgaar aaccaycgtt g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 2
ctccartctt cgryttacaa g                                              21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 3
ccatccaaca tctcagcatg atgaaa                                         26

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer -continued

```
<400> SEQUENCE: 4
cctgaagtag gaaccagatg                                                    20

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 5
ctacgcctgt ctgagtgtc                                                     19

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
atatgcttaa attcagcggg                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 7
tctttccgca gcacaacgtg g                                                  21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 8
catatgaata ccctcagtac tacc                                               24

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 9
aaactgggat tagataccccc actat                                             25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 10
agagtgacgg gcggtgtgt                                                     19

<210> SEQ ID NO 11
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 11
cgcctgttta tcaaaaacat                                                     20

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 12
ccggtctgaa ctcagatcac gt                                                  22

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 13
cccactcact gctaactcc                                                      19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 14
ggctaactac aatcatctgc t                                                   21

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 15
tacgcataac ggctctgg                                                       18

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
ctactacacc tcaactacat ct                                                  22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
```

-continued

```
gctcgggctg ctggaatctt                                               20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 18
caacctcatc tgtcgtaaac                                               20

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 19
atactctgcg gacatacttg actg                                          24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
acttgactga ccttcttact                                               20

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 21
cagtctcgtc aaaccaagtc aaa                                           23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 22
ataatcatcc agcataaaca cac                                           23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
cctggtagag ttcgccgtca                                               20

<210> SEQ ID NO 24
<211> LENGTH: 22
<212> TYPE: DNA
<213> ORGANISM: Artificial Sequence
```

```
<220> FEATURE:
<223> OTHER INFORMATION: Description of Artificial Sequence: Primer

<400> SEQUENCE: 24
cgtgttcctt atcattgtgc ct                                              22

<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 25
tcgtagttca gcagtcag                                                   18

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 26
caccagccaa gtatgtttct c                                               21

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 27
gcctccatca tccctcacct tac                                             23

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 28
ctattcgcct cgctcagac                                                  19

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 29
ctccgtccgt ctcgcctctg                                                 20

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 30
aaatccgccc ttatgtgtgt tc                                              22
```

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 31
catcggcttg ctctattcct tg                                          22

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 32
tctatcggcg gcgtatcac                                              19

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 33
ggcgattcta cggcacgggc g                                           21

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 34
aaactggtcc tcaactatgt ca                                          22

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 35
ccgattcagc cacgattccc tc                                          22

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 36
cctaaagccc agataactac a                                           21

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Primer

```
<400> SEQUENCE: 37
cgtgttctga tgatgatgtg ct                                              22

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 38
attccttcct cttagtatg                                                  19

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 39
gctgaactta ctatgcccta ct                                              22

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
ccgattgacg ccgaactatg                                                 20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41
ttgtacacac cgcccgtcgc                                                 20

<210> SEQ ID NO 42
<211> LENGTH: 747
<212> TYPE: DNA
<213> ORGANISM: Unknown Organism
<220> FEATURE:
<223> OTHER INFORMATION: Description of Unknown Organism: Nucleotide
      sequence of PSL CYTL
<221> NAME/KEY: modified_base
<222> LOCATION: (4)
<223> OTHER INFORMATION: A, T, C, G, other or unknown
<221> NAME/KEY: modified_base
<222> LOCATION: (21)
<223> OTHER INFORMATION: A, T, C, G, other or unknown
<221> NAME/KEY: modified_base
<222> LOCATION: (24)
<223> OTHER INFORMATION: A, T, C, G, other or unknown
<221> NAME/KEY: modified_base
<222> LOCATION: (29)
<223> OTHER INFORMATION: A, T, C, G, other or unknown
<221> NAME/KEY: modified_base
<222> LOCATION: (35)
<223> OTHER INFORMATION: A, T, C, G, other or unknown
<221> NAME/KEY: modified_base
<222> LOCATION: (50)
<223> OTHER INFORMATION: A, T, C, G, other or unknown
```

```
<221> NAME/KEY: modified_base
<222> LOCATION: (59)
<223> OTHER INFORMATION: A, T, C, G, other or unknown
<221> NAME/KEY: modified_base
<222> LOCATION: (62)
<223> OTHER INFORMATION: A, T, C, G, other or unknown
<221> NAME/KEY: modified_base
<222> LOCATION: (65)
<223> OTHER INFORMATION: A, T, C, G, other or unknown
<221> NAME/KEY: modified_base
<222> LOCATION: (72)
<223> OTHER INFORMATION: A, T, C, G, other or unknown
<221> NAME/KEY: modified_base
<222> LOCATION: (83)
<223> OTHER INFORMATION: A, T, C, G, other or unknown
<221> NAME/KEY: modified_base
<222> LOCATION: (85)
<223> OTHER INFORMATION: A, T, C, G, other or unknown
<221> NAME/KEY: modified_base
<222> LOCATION: (87)
<223> OTHER INFORMATION: A, T, C, G, other or unknown
<221> NAME/KEY: modified_base
<222> LOCATION: (95)
<223> OTHER INFORMATION: A, T, C, G, other or unknown
<221> NAME/KEY: modified_base
<222> LOCATION: (102)
<223> OTHER INFORMATION: A, T, C, G, other or unknown
<221> NAME/KEY: modified_base
<222> LOCATION: (109)
<223> OTHER INFORMATION: A, T, C, G, other or unknown
<221> NAME/KEY: modified_base
<222> LOCATION: (122)
<223> OTHER INFORMATION: A, T, C, G, other or unknown
<221> NAME/KEY: modified_base
<222> LOCATION: (144)
<223> OTHER INFORMATION: A, T, C, G, other or unknown
<221> NAME/KEY: modified_base
<222> LOCATION: (216)
<223> OTHER INFORMATION: A, T, C, G, other or unknown
<221> NAME/KEY: modified_base
<222> LOCATION: (218)
<223> OTHER INFORMATION: A, T, C, G, other or unknown
<221> NAME/KEY: modified_base
<222> LOCATION: (220)
<223> OTHER INFORMATION: A, T, C, G, other or unknown
<221> NAME/KEY: modified_base
<222> LOCATION: (226)
<223> OTHER INFORMATION: A, T, C, G, other or unknown
<221> NAME/KEY: modified_base
<222> LOCATION: (236)
<223> OTHER INFORMATION: A, T, C, G, other or unknown
<221> NAME/KEY: modified_base
<222> LOCATION: (309)
<223> OTHER INFORMATION: A, T, C, G, other or unknown
<221> NAME/KEY: modified_base
<222> LOCATION: (327)
<223> OTHER INFORMATION: A, T, C, G, other or unknown
<221> NAME/KEY: modified_base
<222> LOCATION: (331)
<223> OTHER INFORMATION: A, T, C, G, other or unknown
<221> NAME/KEY: modified_base
<222> LOCATION: (371)
<223> OTHER INFORMATION: A, T, C, G, other or unknown
<221> NAME/KEY: modified_base
<222> LOCATION: (387)
<223> OTHER INFORMATION: A, T, C, G, other or unknown
<221> NAME/KEY: modified_base
<222> LOCATION: (392)
<223> OTHER INFORMATION: A, T, C, G, other or unknown
<221> NAME/KEY: modified_base
<222> LOCATION: (397)
<223> OTHER INFORMATION: A, T, C, G, other or unknown
<221> NAME/KEY: modified_base
<222> LOCATION: (409)
<223> OTHER INFORMATION: A, T, C, G, other or unknown
<221> NAME/KEY: modified_base
<222> LOCATION: (467)
<223> OTHER INFORMATION: A, T, C, G, other or unknown
<221> NAME/KEY: modified_base
```

<222> LOCATION: (497)
<223> OTHER INFORMATION: A, T, C, G, other or unknown
<221> NAME/KEY: modified_base
<222> LOCATION: (507)..(508)
<223> OTHER INFORMATION: A, T, C, G, other or unknown
<221> NAME/KEY: modified_base
<222> LOCATION: (517)
<223> OTHER INFORMATION: A, T, C, G, other or unknown
<221> NAME/KEY: modified_base
<222> LOCATION: (523)
<223> OTHER INFORMATION: A, T, C, G, other or unknown
<221> NAME/KEY: modified_base
<222> LOCATION: (546)
<223> OTHER INFORMATION: A, T, C, G, other or unknown
<221> NAME/KEY: modified_base
<222> LOCATION: (556)
<223> OTHER INFORMATION: A, T, C, G, other or unknown
<221> NAME/KEY: modified_base
<222> LOCATION: (591)
<223> OTHER INFORMATION: A, T, C, G, other or unknown
<221> NAME/KEY: modified_base
<222> LOCATION: (634)
<223> OTHER INFORMATION: A, T, C, G, other or unknown
<221> NAME/KEY: modified_base
<222> LOCATION: (644)
<223> OTHER INFORMATION: A, T, C, G, other or unknown
<221> NAME/KEY: modified_base
<222> LOCATION: (646)
<223> OTHER INFORMATION: A, T, C, G, other or unknown
<221> NAME/KEY: modified_base
<222> LOCATION: (656)
<223> OTHER INFORMATION: A, T, C, G, other or unknown
<221> NAME/KEY: modified_base
<222> LOCATION: (679)
<223> OTHER INFORMATION: A, T, C, G, other or unknown
<221> NAME/KEY: modified_base
<222> LOCATION: (689)
<223> OTHER INFORMATION: A, T, C, G, other or unknown
<221> NAME/KEY: modified_base
<222> LOCATION: (699)
<223> OTHER INFORMATION: A, T, C, G, other or unknown
<221> NAME/KEY: modified_base
<222> LOCATION: (708)
<223> OTHER INFORMATION: A, T, C, G, other or unknown
<221> NAME/KEY: modified_base
<222> LOCATION: (717)..(718)
<223> OTHER INFORMATION: A, T, C, G, other or unknown
<221> NAME/KEY: modified_base
<222> LOCATION: (720)
<223> OTHER INFORMATION: A, T, C, G, other or unknown
<221> NAME/KEY: modified_base
<222> LOCATION: (728)
<223> OTHER INFORMATION: A, T, C, G, other or unknown
<221> NAME/KEY: modified_base
<222> LOCATION: (732)
<223> OTHER INFORMATION: A, T, C, G, other or unknown
<221> NAME/KEY: modified_base
<222> LOCATION: (747)
<223> OTHER INFORMATION: A, T, C, G, other or unknown

<400> SEQUENCE: 42

```
cttncccatt ttgggcgctt nggcncgctn ctccncgaga ctctgcgtan taatccaant      60
cnctncgggc cnctccctac cantncncta caccncaaat tncaacccng tttcctcatc     120
antcaaccac atctgtcgaa aacntcaact acggctgact aatccgaaaa catgcacgct     180
aacggtgcct ctttcttctt catctgtatt tatctncncn ttggangagg actatnctac     240
ggatcctacc tctacgaaga gacgtgaggt gttggtgtta ttcttctcct tctaataatg     300
atgactgcnt ttgttggcta tgtgctnccc ngaggacaaa tgtcctttg aggtgctact      360 gtcattacaa ncctactctc tgctgtnccg tntgttngcg gcntctant tcaatgaatt      420 tgaggtggct tctccgtaaa cacgcaacgc tcactcgttt cttcgcnttc cacttcttgt     480
tcccatttgt tgtcgcngct ataaccnngg ttcaccngat ttnccgacat caaacaggct     540
```

```
ctaaanccccc cccggnttga ctccatacaa caaaaccctc caccctattc nctataaaac      600
tctaggttcg tgcccgtatt ggcttacttc atgnctattt cccngncgga gggacnaaaa      660
ttcctgcacc ccctccccnc aaaataaana atgtgtctnt cctaccanaa aacaacnnan      720
acggggtntg cncttccatc atccacn                                          747
```

```
<210> SEQ ID NO 43
<211> LENGTH: 225
<212> TYPE: DNA
<213> ORGANISM: Unknown Organism
<220> FEATURE:
<223> OTHER INFORMATION: Description of Unknown Organism: Nucleotide
      sequence of PSLITS2F
<221> NAME/KEY: modified_base
<222> LOCATION: (17)
<223> OTHER INFORMATION: A, T, C, G, other or unknown
<221> NAME/KEY: modified_base
<222> LOCATION: (21)..(22)
<223> OTHER INFORMATION: A, T, C, G, other or unknown

<400> SEQUENCE: 43
tctacgatct accggcnttt nntgtggaaa gacgatcatg catttatgtg tgtctttcta       60
tggatttgaa ccgtgtggta cgtctttgcg tactgcttgg aaggctcaac ttgcttctgt     120
ccttctcttg cagtctcgca ctgtctatgc aacgtgttct acttcgactt ctgtcgaaaa     180
atcttacttt tgacctcaga tcagacaaga ctacccgctg aattt                    225
```

```
<210> SEQ ID NO 44
<211> LENGTH: 750
<212> TYPE: DNA
<213> ORGANISM: Unknown Organism
<220> FEATURE:
<223> OTHER INFORMATION: Description of Unknown Organism: Nucleotide
      sequence of PSL PROL
<221> NAME/KEY: modified_base
<222> LOCATION: (10)
<223> OTHER INFORMATION: A, T, C, G, other or unknown
<221> NAME/KEY: modified_base
<222> LOCATION: (20)
<223> OTHER INFORMATION: A, T, C, G, other or unknown
<221> NAME/KEY: modified_base
<222> LOCATION: (292)
<223> OTHER INFORMATION: A, T, C, G, other or unknown
<221> NAME/KEY: modified_base
<222> LOCATION: (424)
<223> OTHER INFORMATION: A, T, C, G, other or unknown
<221> NAME/KEY: modified_base
<222> LOCATION: (434)
<223> OTHER INFORMATION: A, T, C, G, other or unknown
<221> NAME/KEY: modified_base
<222> LOCATION: (498)
<223> OTHER INFORMATION: A, T, C, G, other or unknown
<221> NAME/KEY: modified_base
<222> LOCATION: (500)
<223> OTHER INFORMATION: A, T, C, G, other or unknown
<221> NAME/KEY: modified_base
<222> LOCATION: (556)
<223> OTHER INFORMATION: A, T, C, G, other or unknown
<221> NAME/KEY: modified_base
<222> LOCATION: (562)
<223> OTHER INFORMATION: A, T, C, G, other or unknown
<221> NAME/KEY: modified_base
<222> LOCATION: (604)
<223> OTHER INFORMATION: A, T, C, G, other or unknown
<221> NAME/KEY: modified_base
<222> LOCATION: (612)
<223> OTHER INFORMATION: A, T, C, G, other or unknown
<221> NAME/KEY: modified_base
<222> LOCATION: (621)
<223> OTHER INFORMATION: A, T, C, G, other or unknown
```

```
<221> NAME/KEY: modified_base
<222> LOCATION: (631)
<223> OTHER INFORMATION: A, T, C, G, other or unknown
<221> NAME/KEY: modified_base
<222> LOCATION: (634)
<223> OTHER INFORMATION: A, T, C, G, other or unknown
<221> NAME/KEY: modified_base
<222> LOCATION: (643)..(644)
<223> OTHER INFORMATION: A, T, C, G, other or unknown
<221> NAME/KEY: modified_base
<222> LOCATION: (651)
<223> OTHER INFORMATION: A, T, C, G, other or unknown
<221> NAME/KEY: modified_base
<222> LOCATION: (656)..(658)
<223> OTHER INFORMATION: A, T, C, G, other or unknown
<221> NAME/KEY: modified_base
<222> LOCATION: (663)..(664)
<223> OTHER INFORMATION: A, T, C, G, other or unknown
<221> NAME/KEY: modified_base
<222> LOCATION: (666)
<223> OTHER INFORMATION: A, T, C, G, other or unknown
<221> NAME/KEY: modified_base
<222> LOCATION: (675)
<223> OTHER INFORMATION: A, T, C, G, other or unknown
<221> NAME/KEY: modified_base
<222> LOCATION: (680-683)
<223> OTHER INFORMATION: A, T, C, G, other or unknown
<221> NAME/KEY: modified_base
<222> LOCATION: (688)
<223> OTHER INFORMATION: A, T, C, G, other or unknown
<221> NAME/KEY: modified_base
<222> LOCATION: (695)
<223> OTHER INFORMATION: A, T, C, G, other or unknown
<221> NAME/KEY: modified_base
<222> LOCATION: (708)
<223> OTHER INFORMATION: A, T, C, G, other or unknown
<221> NAME/KEY: modified_base
<222> LOCATION: (710)..(711)
<223> OTHER INFORMATION: A, T, C, G, other or unknown
<221> NAME/KEY: modified_base
<222> LOCATION: (725)..(726)
<223> OTHER INFORMATION: A, T, C, G, other or unknown
<221> NAME/KEY: modified_base
<222> LOCATION: (732)
<223> OTHER INFORMATION: A, T, C, G, other or unknown
<221> NAME/KEY: modified_base
<222> LOCATION: (735)..(737)
<223> OTHER INFORMATION: A, T, C, G, other or unknown
<221> NAME/KEY: modified_base
<222> LOCATION: (750)
<223> OTHER INFORMATION: A, T, C, G, other or unknown

<400> SEQUENCE: 44 cctttcggn ataggcccan ctcaaatgaa ttccttctct cctggtccaa gcccaaactg     60
tggacggcag gttgacaatg gttacaaatc gtgacaaatc ggctacataa ttgccgatag    120
cgatgtcgtc aaaccaagtc aaacaatggc cgatgtatat cggccaaacc catatatggg    180
tctggctgta gtttgtgttg agcaacgtca caccagtgtc tggtcagcat ataagatgtt    240
gacatcttgc aacatcttac ccacagacag acagttacgg ctgcttacga anggcgctag    300
tgttgtggtg agaaacgaag atacatacgt caaacgacg ccggtgcact tgaagacact    360
gtttgaaggt gccgcactac ttgacagaca gcccatgatg cgctggacag tgaccaaagc    420
tacnggagga ccanatggaa atcctgttgg cgttgccgtg ggactcaagt tgtacactt     480 tggatggttg atcactanan ccgctgccgg gagaagcact cgctcctggt tcactaatca    540
gattgaggtt aaccanattg angtaaacat cttcaacaca gtgtctttat gctggatgaa    600
attnagccca cnggacacca naaaagaatt nccnctggtt ctnncggggg ncccnnnaa    660 cgnntnttcc ccttntctcn nnngcggnga agttnccccc ccccactnan ntcttccttc    720
aananntttc cnccnnnaga ggttttcccn                                    750
```

<210> SEQ ID NO 45
<211> LENGTH: 748
<212> TYPE: DNA
<213> ORGANISM: Unknown Organism
<220> FEATURE:
<223> OTHER INFORMATION: Description of Unknown Organism: Nucleotide sequence of ROD PSL SLMB
<221> NAME/KEY: modified_base
<222> LOCATION: (43)
<223> OTHER INFORMATION: A, T, C, G, other or unknown
<221> NAME/KEY: modified_base
<222> LOCATION: (280)
<223> OTHER INFORMATION: A, T, C, G, other or unknown
<221> NAME/KEY: modified_base
<222> LOCATION: (470)
<223> OTHER INFORMATION: A, T, C, G, other or unknown
<221> NAME/KEY: modified_base
<222> LOCATION: (483)
<223> OTHER INFORMATION: A, T, C, G, other or unknown
<221> NAME/KEY: modified_base
<222> LOCATION: (486)
<223> OTHER INFORMATION: A, T, C, G, other or unknown
<221> NAME/KEY: modified_base
<222> LOCATION: (493)
<223> OTHER INFORMATION: A, T, C, G, other or unknown
<221> NAME/KEY: modified_base
<222> LOCATION: (497)
<223> OTHER INFORMATION: A, T, C, G, other or unknown
<221> NAME/KEY: modified_base
<222> LOCATION: (503)
<223> OTHER INFORMATION: A, T, C, G, other or unknown
<221> NAME/KEY: modified_base
<222> LOCATION: (505)
<223> OTHER INFORMATION: A, T, C, G, other or unknown
<221> NAME/KEY: modified_base
<222> LOCATION: (516)
<223> OTHER INFORMATION: A, T, C, G, other or unknown
<221> NAME/KEY: modified_base
<222> LOCATION: (520)
<223> OTHER INFORMATION: A, T, C, G, other or unknown
<221> NAME/KEY: modified_base
<222> LOCATION: (523)
<223> OTHER INFORMATION: A, T, C, G, other or unknown
<221> NAME/KEY: modified_base
<222> LOCATION: (525)..(526)
<223> OTHER INFORMATION: A, T, C, G, other or unknown
<221> NAME/KEY: modified_base
<222> LOCATION: (633)
<223> OTHER INFORMATION: A, T, C, G, other or unknown
<221> NAME/KEY: modified_base
<222> LOCATION: (636)
<223> OTHER INFORMATION: A, T, C, G, other or unknown
<221> NAME/KEY: modified_base
<222> LOCATION: (639)
<223> OTHER INFORMATION: A, T, C, G, other or unknown
<221> NAME/KEY: modified_base
<222> LOCATION: (643)
<223> OTHER INFORMATION: A, T, C, G, other or unknown
<221> NAME/KEY: modified_base
<222> LOCATION: (651)
<223> OTHER INFORMATION: A, T, C, G, other or unknown
<221> NAME/KEY: modified_base
<222> LOCATION: (656)
<223> OTHER INFORMATION: A, T, C, G, other or unknown
<221> NAME/KEY: modified_base
<222> LOCATION: (661)
<223> OTHER INFORMATION: A, T, C, G, other or unknown
<221> NAME/KEY: modified_base
<222> LOCATION: (687)..(688)
<223> OTHER INFORMATION: A, T, C, G, other or unknown
<221> NAME/KEY: modified_base
<222> LOCATION: (690)
<223> OTHER INFORMATION: A, T, C, G, other or unknown
<221> NAME/KEY: modified_base
<222> LOCATION: (699)
<223> OTHER INFORMATION: A, T, C, G, other or unknown
<221> NAME/KEY: modified_base -continued

```
<222> LOCATION: (714)
<223> OTHER INFORMATION: A, T, C, G, other or unknown
<221> NAME/KEY: modified_base
<222> LOCATION: (717)
<223> OTHER INFORMATION: A, T, C, G, other or unknown
<221> NAME/KEY: modified_base
<222> LOCATION: (735)
<223> OTHER INFORMATION: A, T, C, G, other or unknown

<400> SEQUENCE: 45
cctggtaggg ttccccgtca acttcctcac actgtacctc acnttcgagc acaagaagct      60 actaacccc  ttaaactaca tcctgctcaa cctggcggtc ggagacctcc tgatggtgta     120
aggagggttc accaccacca tctacacctc catgcacggc tacttcgtcc tagggaaact    180
gggctgcgcc atcgaaggtt tcatggccac ccatggtggt caggtcgccc tttggtccct    240
ggtggttttg gccgtggaaa ggtggctggt cgtctgcaan cccatctcca gcttccgctt    300
ccaggagtcc cactccctca tgggcctggc cgtgacctgg gtgatggcga cggcttgttc    360
tgtgcccccc ctgggtcggc tggtctcgct acatcccaga aggcatgcag tgctcatgcg    420
gaatggacta ctacactccc gcgccgggcg tcaacaatga atcctacgtn gtgtacatgt    480
tcntcanaaa aanaatngga ccncnggcg atcatnttgn tangnnaagg ccagntgntg     540
ngagcagtca aggcggccgc cgccgcccag caagagtccg agaccaccca gagggccgag    600
agggaagtca cccgnatggt natnangatg gtnatntcnt tcntggtaag nagggngcca    660
nacgccagcg tggcctggtg gatcttnngn aaccagggng cagaattagg cccngtnttc    720
atgaccctgc cggcnttctt tgccaaga                                       748
```

What is claimed is:

1. A method for developing nucleotide probes for myctophid fishes, said method comprising the steps of:
(i) extracting DNA from the muscle tissue of a myctophid fish,
(ii) selecting a gene region in the extracted DNA as a DNA template and amplifying the selected gene region with the a pair of forward and backward selected primers using polymerase chain reaction (PCR),
(iii) eluting the amplified DNA containing the selected gene region,
(iv) re-amplifying and re-eluting the amplified DNA in step (iii),
(v) cycle sequencing the of eluted DNA containing the selected gene region using a single primer to produce an extension product,
(vi) purifying the extension product containing the selected gene region,
(vii) sequencing the nucleotides of the extension product of step (vi) on an acrylamide gel,
(viii) confirming the nucleotide sequence of the selected gene region by Blast-Email,
(ix) ligating the extension product containing the selected gene region as a DNA insert into a cloning vector,
(x) preparing host cells for electro-transformation,
(xi) electro-transforming the host cells with the vector-containing DNA insert,
(xii) growing and harvesting of transformed host cells,
(xiii) re-inoculating and growing transformed host cells that appear as white colonies and that express the DNA insert containing the selected gene region;
(xiv) confirming the presence of the DNA insert containing the selected gene region by polymerase chain reaction,
(xv) purifying the cloned DNA insert containing the selected gene region from the transformed host cells to produce a DNA probe,
(xvi) checking the purity and specificity of the DNA probe by cutting with a restriction enzyme,
(xvii) confirming the molecular size of the DNA probe,
(xviii) amplifying the DNA probe using the selected set of forward and backward primers of step (ii),
(xix) eluting the amplified DNA probe containing the selected gene region,
(xx) cycle sequencing the eluted DNA probe in step (xix) using a single set of primer,
(xxi) sequencing the eluted DNA probe in step (xix) on an acrylamide gel,
(xxii) comparing the nucleotide sequence of the DNA probe using "BLAST program" against the known sequences of similar genes in the genome data bases,
(xxiii) confirming the sequence of the DNA probe by aligning with sequence obtained in step (vii), and
(xxiv) designing species specific primers based on the sequence of the DNA probe, wherein the DNA probe for the D-Loop gene is PSL PROL, wherein the nucleotide base sequence of PSL PROL comprises: (750 BP) (SEQ ID NO:44)

```
5' CCTTTTCGGN ATAGGCCCAN CTCAAATGAA TTCCTTCTCT

CCTGGTCCAA GCCCAAACTG TGGACGGCAG GTTGACAATG

GTTACAAATC GTGACAAATC GGCTACATAA TTGCCGATAG

CGATGTCGTC AAACCAAGTC AAACAATGGC CGATGTATAT

CGGCCAAACC CATATATGGG TCTGGCTGTA GTTTGTGTTG

AGCAACGTCA CACCAGTGTC TGGTCAGCAT ATAAGATGTT

GACATCTTGC AACATCTTAC CCACAGACAG ACAGTTACGG

CTGCTTACGA ANGGCGCTAG TGTTGTGGTG AGAAACGAAG

ATACATACGT CAAACAGACG CCGGTGCACT TGAAGACACT

GTTTGAAGGT GCCGCACTAC TTGACAGACA GCCCATGATG

CGCTGGACAG TGACCAAAGC TACNGGAGGA CCANATGGAA
```

-continued

```
  ATCCTGTTGG CGTTGCCGTG GGACTCAAGT TGTACACTTT

TGGATGGTTG ATCACTANAN CCGCTGCCGG GAGAAGCACT

CGCTCCTGGT TCACTAATCA GATTGAGGTT AACCANATTG

ANGTAAACAT CTTCAACACA GTGTCTTTAT GCTGGATGAA

ATTNAGCCCA CNGGACACCA NAAAAGAATT NCCNCTGGTT

CTNNCGGGGG NCCCCNNNAA CGNNTNTTCC CCTTNTCTCN

NNNGCGGNGA AGTTNCCCCC CCCCACTNAN NTCTTCCTTC

AANANNTTTC CNCCNNNAGA GGTTTTCCCN 3'.
```

2. A polynuicleotide sequence comprising SEQ ID NO: 44.

\* \* \* \* \*